United States Patent
Liu et al.

(10) Patent No.: US 10,905,656 B2
(45) Date of Patent: Feb. 2, 2021

(54) METHODS AND COMPOSITIONS FOR TREATING ARTERIOSCLEROTIC VASCULAR DISEASES

(71) Applicants: GOLDEN BIOTECHNOLOGY CORPORATION, New Jersey, NJ (US); Sheng-Yung Liu, New Taipei (TW); Wu-Che Wen, New Taipei (TW); Chih-Ming Chen, New Taipei (TW)

(72) Inventors: Sheng-Yung Liu, New Taipei (TW); Wu-Che Wen, New Taipei (TW); Chih-Ming Chen, New Taipei (TW)

(73) Assignee: Golden Biotechnology Corporation, Jersey City, NJ (US)

( * ) Notice: Subject to any disclaimer, the term of this patent is extended or adjusted under 35 U.S.C. 154(b) by 73 days.

(21) Appl. No.: 14/390,017

(22) PCT Filed: Mar. 26, 2013

(86) PCT No.: PCT/US2013/033900
§ 371 (c)(1),
(2) Date: Oct. 1, 2014

(87) PCT Pub. No.: WO2013/148701
PCT Pub. Date: Oct. 3, 2013

(65) Prior Publication Data
US 2015/0080477 A1 Mar. 19, 2015

Related U.S. Application Data

(60) Provisional application No. 61/615,794, filed on Mar. 26, 2012, provisional application No. 61/789,304, filed on Mar. 15, 2013.

(51) Int. Cl.
| | |
|---|---|
| *A61K 31/122* | (2006.01) |
| *A61P 3/10* | (2006.01) |
| *A61K 36/07* | (2006.01) |
| *A61K 31/133* | (2006.01) |
| *A61P 9/10* | (2006.01) |
| *C07C 49/753* | (2006.01) |
| *A61K 9/00* | (2006.01) |
| *A61K 9/48* | (2006.01) |

(52) U.S. Cl.
CPC .......... *A61K 31/122* (2013.01); *A61K 31/133* (2013.01); *A61K 36/07* (2013.01); *A61P 9/10* (2018.01); *C07C 49/753* (2013.01); *A61K 9/0014* (2013.01); *A61K 9/0031* (2013.01); *A61K 9/0048* (2013.01); *A61K 9/0056* (2013.01); *A61K 9/0078* (2013.01); *A61K 9/4858* (2013.01)

(58) Field of Classification Search
CPC .................. A61K 31/122; A61P 9/10
See application file for complete search history.

(56) References Cited

U.S. PATENT DOCUMENTS

| | | | | |
|---|---|---|---|---|
| 7,342,137 | B1 * | 3/2008 | Liu | C07C 403/02 568/377 |
| 2006/0251673 | A1 * | 11/2006 | Hwang et al. | 424/195.15 |
| 2008/0312335 | A1 * | 12/2008 | Liu et al. | 514/690 |
| 2011/0060058 | A1 * | 3/2011 | Liu et al. | 514/690 |

OTHER PUBLICATIONS

Paoletti et al. (Circulation, 109, 2004, III-20-III-26).*
Yang et al. (Circulation Research, 2004, 95, 1075-1081).*
Shin et al. (The Journal of Korean Oriental Medicine, 2010, 31, 1-7) (Year: 2010).*
Kaliora et al., "Dietary antioxidants in preventing atherogenesis," Atherosclerosis 187(1), 1-17 (2006). PMID: 16313912. (Year: 2006).*
Kalanuria et al., "The prevention and regression of atherosclerotic plaques: emerging treatments," Vasc. Health Risk Manag. 8:549-61 (2012). PMID: 23049260. (Year: 2012).*
Hseu, You-Cheng, et al., "Antioxidant activity of Antrodia camphorata on free radical-induced endothelial cell damage," Journal of Ethnopharmacology, 118 (2008), 237-245.
Tsai, Pei-Yi, et al., "Antroquinonol reduces oxidative stress by enhancing the Nrf2 signaling pathway and inhibits inflammation and sclerosis in focal segmental glomerulosclerosis mice," Free Radical Biology and Medicine, Mar. 2, 2011, 1503-1516.
Li, Yi-Heng, et al., "A novel inhibitory effect of Antrodia Camphorata Extract on Vascular Smooth Muscle Cell Migration and Neointima Formation in Mice," Int. Heart J., 50(2), Mar. 31, 2009, 50(2), 207-219.
Huang, Chia-Hsin, et al., "Fruiting Body of Niuchangchih (Antrodia camphorata) Protects Livers against Chronic Alcohol Consumption Damage," J. Agric. Food Chem., 2010, 58, 3859-3866.

\* cited by examiner

*Primary Examiner* — Theodore R. West
(74) *Attorney, Agent, or Firm* — Chang-Hsing Liang

(57) ABSTRACT

The present invention provides methods and compositions for treating arteriosclerotic vascular diseases by cyclohexenone compounds. In some embodiments, the compound in the methods inhibits PDGF-stimulated smooth muscle cell proliferation or migration. In some embodiments, the atherosclerosis is associated with coronary artery disease, aneurysm, arteriosclerosis, myocardial infarction, embolism, stroke, thrombosis, angina, vascular plaque inflammation, vascular plaque rupture, Kawasaki disease, calcification or inflammation. In some embodiments, the compound lowers low-density lipoprotein (LDL) cholesterol in the subject. In some embodiments, the compound maintains a normal low-density lipoprotein (LDL) cholesterol level in the subject.

19 Claims, 11 Drawing Sheets
Specification includes a Sequence Listing.

FIG. 2A/2B
2A
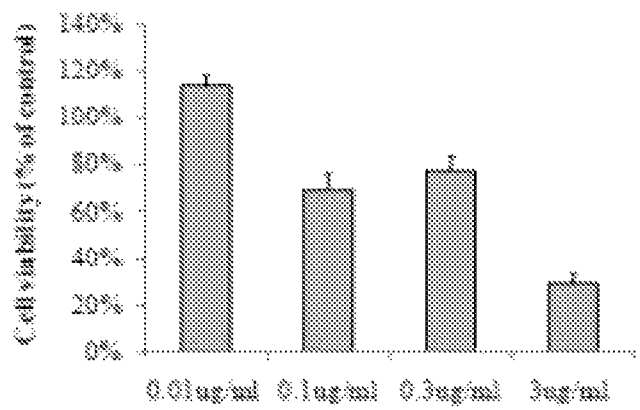
2B
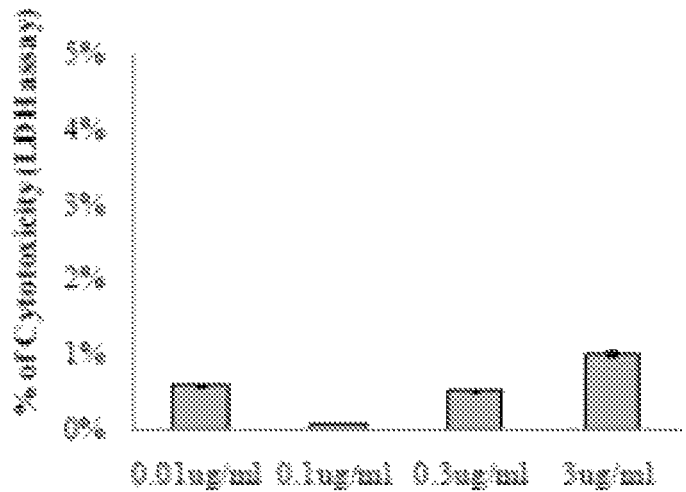

FIG. 4
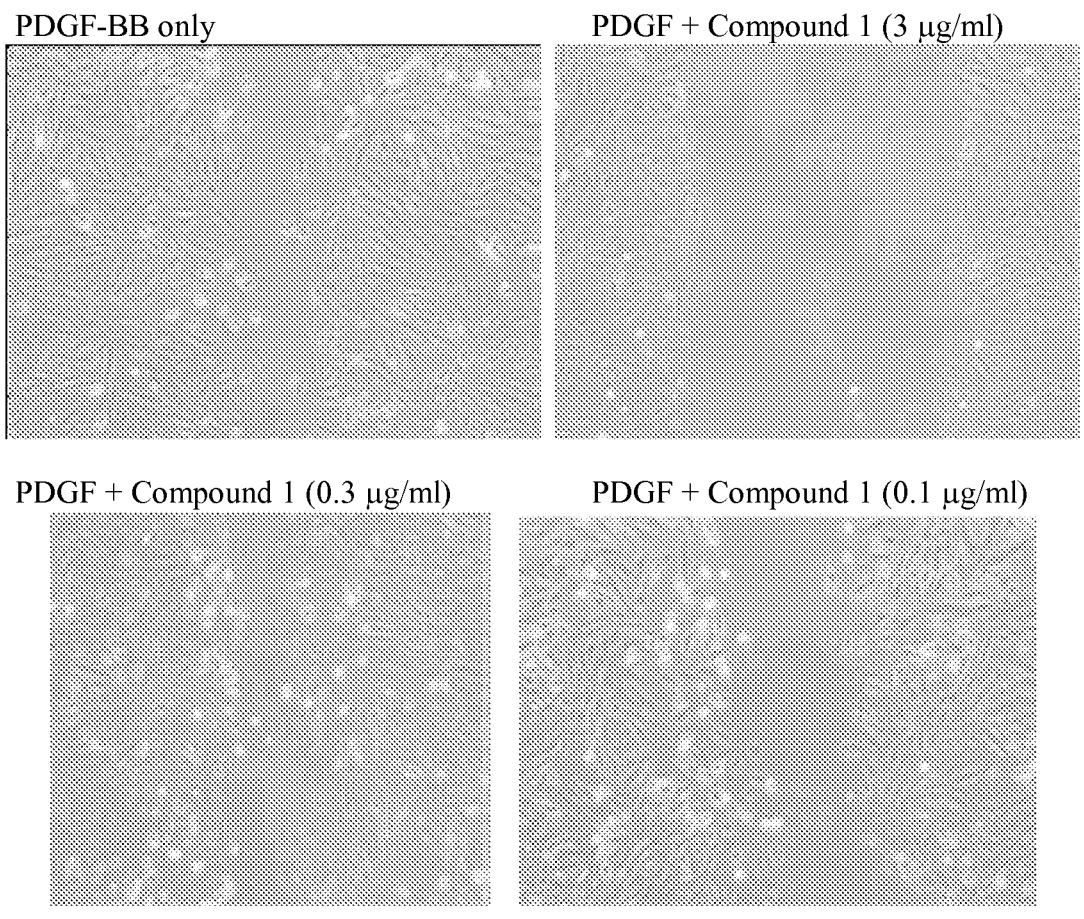
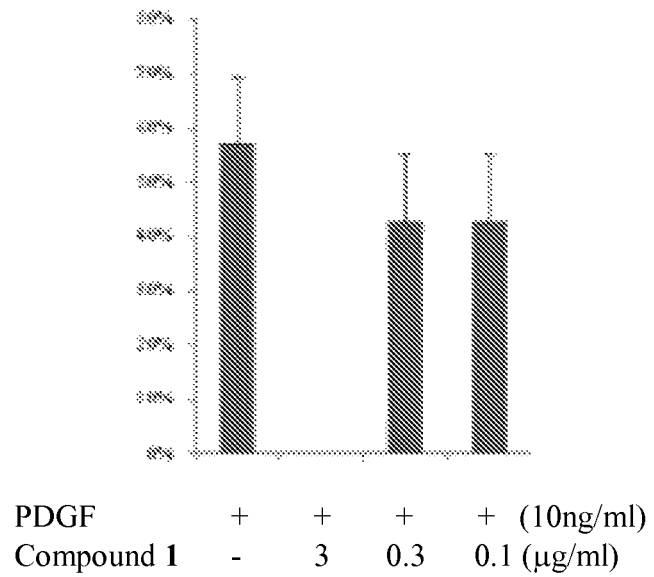
PDGF          +     +     +     +    (10ng/ml)
Compound 1    -     3    0.3   0.1  (μg/ml)

FIG. 5
Ligation
Ligation + Compound 1 (60 mg/Kg)
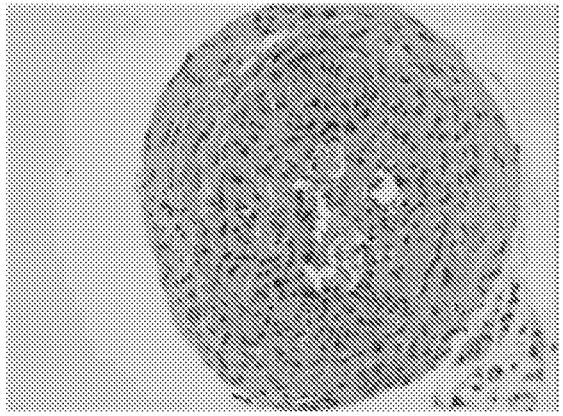
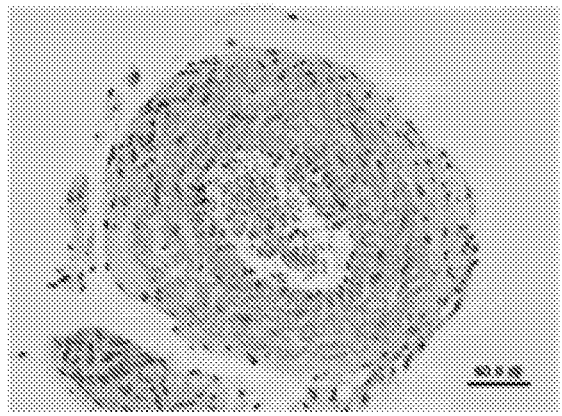

FIG. 6
Ligation
Ligation + Compound 1 (60 mg/Kg)
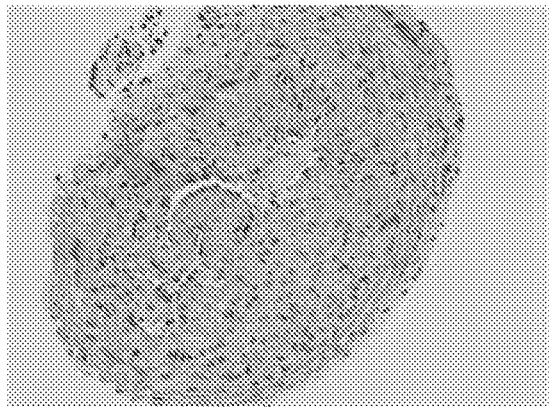
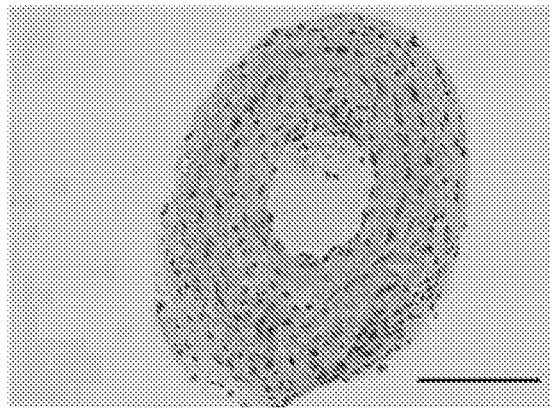

FIG. 10A/B
A
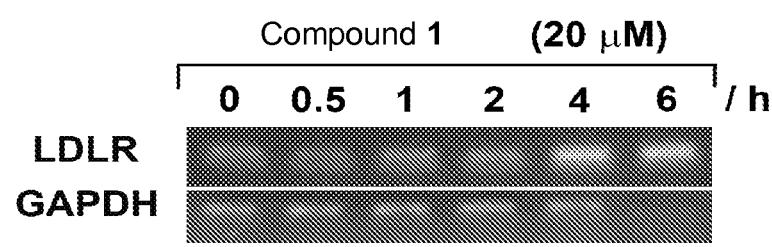
B
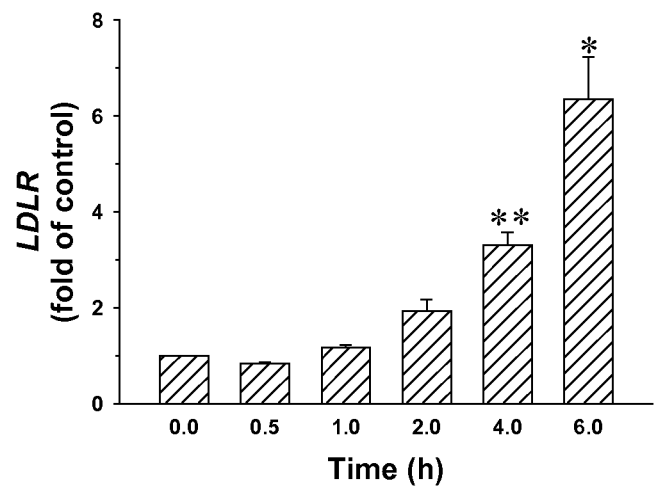

FIG. 11A/B
A
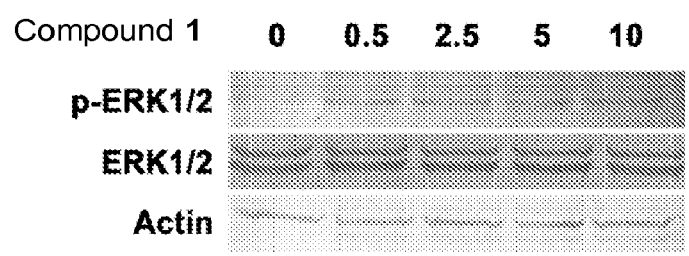
B
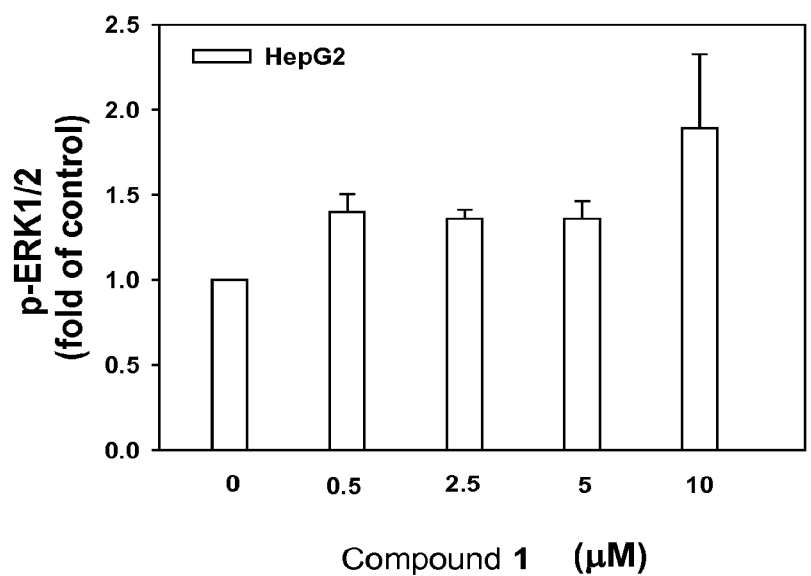

SEQUENCE LISTING

```
<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctttcaacac acaacagcag a                                              21

<210> SEQ ID NO 2
<211> LENGTH: 19
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 2
tgacagggca aaggctaac                                                19

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggtatcgtgg aaggactcat                                               20

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccttgcccac agccttg                                                  17

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tttttttttt tttttttttt                                               20
```

METHODS AND COMPOSITIONS FOR TREATING ARTERIOSCLEROTIC VASCULAR DISEASES

CROSS REFERENCE

This application claims the benefit of U.S. Provisional Application No. 61/615,794, filed Mar. 26, 2012, and U.S. Provisional Application No. 61/789,304, filed Mar. 15, 2013, each of which is hereby incorporated by reference.

SEQUENCE LISTING

The instant application contains a Sequence Listing that has been submitted via EFS-Web and is hereby incorporated by reference in its entirety. Said ASCII copy, created on Oct. 1, 2014, is named GBC713US.TXT, and is 1,491 bytes in size.

BACKGROUND OF THE INVENTION

Atherosclerosis (also known as arteriosclerotic vascular disease or ASVD) is a condition in which an artery wall thickens as a result of the accumulation of fatty materials such as cholesterol. It is a syndrome affecting arterial blood vessels, a chronic inflammatory response in the walls of arteries, caused largely by the accumulation of macrophage white blood cells and promoted by low-density lipoproteins (plasma proteins that carry cholesterol and triglycerides) without adequate removal of fats and cholesterol from the macrophages by functional high density lipoproteins (HDL), (see apoA-1 Milano). It is commonly referred to as a hardening or furring of the arteries. It is caused by the formation of multiple plaques within the arteries. Atherosclerosis affects the entire artery tree, but mostly larger, high-pressure vessels such as the coronary, renal, femoral, cerebral, and carotid arteries.

Low-density lipoprotein (LDL) is one of the five major groups of lipoproteins, which in order of size, largest to smallest, are chylomicrons, VLDL, IDL, LDL, and HDL. Studies have shown that higher levels of LDL particles (such as LDL-c, cholesterol in LDL) promote health problems and cardiovascular disease, they are often informally called the bad cholesterol particles, (as opposed to HDL particles, which are frequently referred to as good cholesterol or healthy cholesterol particles).

Atherosclerotic lesions, or atherosclerotic plaques are separated into two broad categories: Stable and unstable (also called vulnerable). The pathobiology of atherosclerotic lesions is very complicated but generally, stable atherosclerotic plaques, which tend to be asymptomatic, are rich in extracellular matrix and smooth muscle cells, while, unstable plaques are rich in macrophages and foam cells and the extracellular matrix separating the lesion from the arterial lumen (also known as the fibrous cap) is usually weak and prone to rupture. Ruptures of the fibrous cap, expose thrombogenic material, such as collagen to the circulation and eventually induce thrombus formation in the lumen. Upon formation, intraluminal thrombi can occlude arteries outright (i.e. coronary occlusion), but more often they detach, move into the circulation and eventually occlude smaller downstream branches causing thromboembolism (i.e. Stroke is often caused by thrombus formation in the carotid arteries). Apart from thromboembolism, chronically expanding atherosclerotic lesions can cause complete closure of the lumen. Interestingly, chronically expanding lesions are often asymptomatic until lumen stenosis is so severe that blood supply to downstream tissue(s) is insufficient resulting in ischemia.

PDGF functions as a primary mitogen and chemoattractant for cells of mesenchymal origin. Members of the PDGF family play an important role during embryonic development and contribute to the maintenance of connective tissue in adults. Deregulation of PDGF signaling has been linked to atherosclerosis, pulmonary hypertension and organ fibrosis.

SUMMARY OF THE INVENTION

In one aspect provides herein for the treatment of atherosclerosis comprising administering to a subject a therapeutically effective amount of a cyclohexenone compound having the structure:

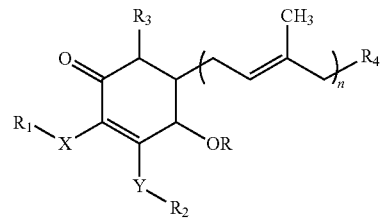

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

In another aspect provides herein methods of inhibiting the production or progression of one or more atherosclerotic lesions within the vasculature of a subject, comprising administering to the subject in need a therapeutically effective amount of a cyclohexenone compound having the structure:

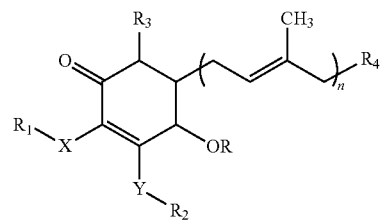

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

In another aspect provides herein methods for preventing or treating an inflammation-related arteriosclerotic vascular disease in a subject comprising administering to the subject a therapeutically effective amount of a cyclohexenone compound having the structure:

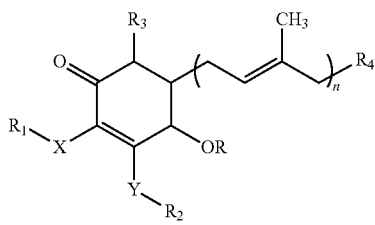

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

In another aspect provides herein methods of reducing C-reactive protein in a subject comprising administering to the subject a therapeutically effective amount of a cyclohexenone compound having the structure:

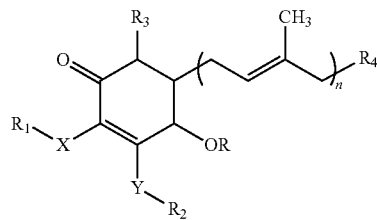

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

In one aspect provides herein methods of lowering low-density lipoprotein (LDL) cholesterol in a subject comprising administering to the subject a therapeutically effective amount of a compound having the structure:

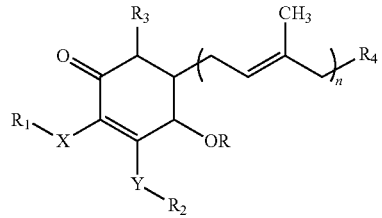

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

In another aspect provides herein methods of maintaining a normal low-density lipoprotein (LDL) cholesterol level in a subject comprising administering to the subject a therapeutically effective amount of a compound having the structure:

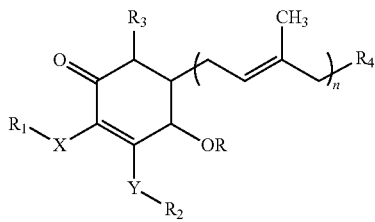

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A-B show illustrative results of cytotoxic effect of Compound 1 at different concentrations on smooth muscle cells (A7r5) via MTT assay (2A) and LDH assay (2B).

FIG. 4 provides illustrative results of 24-hour examination of PDGF-stimulated smooth muscle cell migration exposed to Compound 1 at different concentrations. * P<0.05 compared with 10 ng/ml PDGF.

FIG. 5 shows illustrative results of pathologic analysis of carotid artery in media area after treatment of Compound 1 under 400× microscope.

FIG. 6. shows illustrative results of pathologic analysis of carotid artery in neointima area after treatment of Compound 1 under 400× microscope.

FIG. 10A-B show results of LDLR mRNA expression in HepG2 cell line induced by an exemplary cyclohexenone Compound 1. HepG2 cell line was serum-starved overnight and challenged with 20 μM Compound 1 at indicated time intervals (1A). Cells were then collected and the mRNA expression level of LDLR and GAPDH (internal control) were detected by RT-PCR. The relative expression level of LDLR to GAPDH was quantified by densitometry (1B). Experiments were conducted in triplicate. Bar represented as mean±SEM. * indicates p<0.05 and ** indicates p<0.01.

FIG. 11A-B show illustrative effective results of the exemplary cyclohexenone Compound 1 stimulates ERK1/2 phosphorylation in HepG2 cell line. (2A), HepG2 cell line was serum-starved overnight and challenged with the indicated concentrations of Compound 1 for 1 h. Whole cell lysates were then immunoblotted with phosphor-ERK1/2 antibody and reprobed with β-actin antibody. Duplicated membrane was probed with ERK1/2 antibody. (2B), the relative expression level of p-ERK1/2 to β-actin was quantified by densitometry. Experiments were conducted in triplicate. Bar represented as mean±SEM.

DETAILED DESCRIPTION OF THE INVENTION

Figure 1:
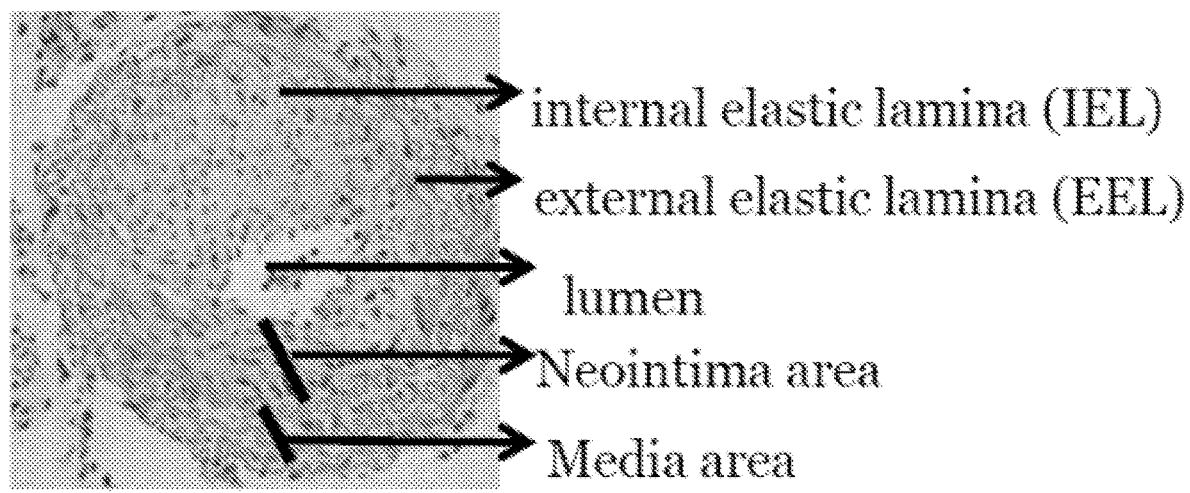
FIG. 1 illustrates cross-section photograph of mouse vessel (HSING-CHUN CHUNG, 2008 Dissertation, title, "Novel inhibitory effect of *Antrodia camphorate* on smooth muscle cell migration and carotid neointima formation in mice").

When atherosclerosis leads to symptoms, some symptoms such as angina pectoris can be treated. Non-pharmaceutical means are usually the first method of treatment, such as cessation of smoking and practicing regular exercise. If these methods do not work, medicines are usually the next step in treating cardiovascular diseases, and, with improvements, have increasingly become the most effective method over the long term. Common medicines for atherosclerosis (or arteriosclerotic vascular disease) include a group of medications referred to as statins. They have relatively few short-term or longer-term undesirable side-effects. The invention cyclohexenone compounds, in some embodiments, are obtained from extracts of natural products and provide reduced complications and/or side effects. In some embodiments, provided herein are methods for the treatment of atherosclerosis by administering a cyclohexenone compound provided herein to a subject (e.g. a human). The cyclohexenone compounds provide therapeutic benefit to a subject being treated for atherosclerosis or its related symptoms such as high LDL cholesterol (see Examples 1-14).

In some embodiments, there are provided methods for the treatment of atherosclerosis comprising administering to a subject a therapeutically effective amount of a cyclohexenone compound having the structure:

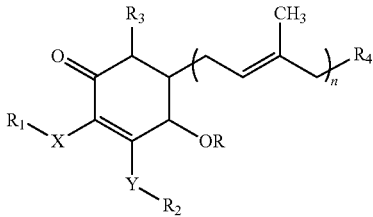

wherein each of X and Y independently is oxygen, $NR_5$ or sulfur;

R is a hydrogen or $C(=O)C_1\text{-}C_8$alkyl;

each of $R_1$, $R_2$ and $R_3$ independently is a hydrogen, methyl or $(CH_2)_m\text{—}CH_3$; $R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1\text{-}C_8$alkyl, $C_2\text{-}C_8$alkenyl, $C_2\text{-}C_8$alkynyl, aryl, glucosyl, wherein the 5 or 6-membered lactone, $C_1\text{-}C_8$alkyl, $C_2\text{-}C_8$alkenyl, $C_2\text{-}C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1\text{-}C_8$ alkyl, $C_2\text{-}C_8$ alkenyl, $C_2\text{-}C_8$ alkynyl, $C_3\text{-}C_8$ cycloalkyl, and $C_1\text{-}C_8$ haloalkyl;

each of $R_5$ and $R_6$ is independently a hydrogen or $C_1\text{-}C_8$alkyl;

$R_7$ is a $C_1\text{-}C_8$alkyl, $OR_5$ or $NR_5R_6$;

m=1-12; and n=1-12; or a pharmaceutically acceptable salt, metabolite, solvate or prodrug thereof.

In some embodiments, the compound in the methods inhibits PDGF-stimulated smooth muscle cell proliferation or migration. In some embodiments, the atherosclerosis is associated with coronary artery disease, aneurysm, arteriosclerosis, myocardial infarction, embolism, stroke, thrombosis, angina, vascular plaque inflammation, vascular plaque rupture, Kawasaki disease, calcification or inflammation. In some embodiments, the compound lowers low-density lipoprotein (LDL) cholesterol in the subject. In some embodiments, the compound maintains a normal low-density lipoprotein (LDL) cholesterol level in the subject. In some embodiments, the subject is human. See Examples 2-14.

In some embodiments, there are provided methods inhibiting the production or progression of one or more atherosclerotic lesions within the vasculature of a subject, comprising administering to the subject in need a therapeutically effective amount of a cyclohexenone compound having the structure:

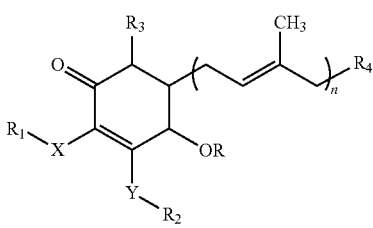

wherein each of X and Y independently is oxygen, $NR_5$ or sulfur;

R is a hydrogen or $C(=O)C_1\text{-}C_8$alkyl;

each of $R_1$, $R_2$ and $R_3$ independently is a hydrogen, methyl or $(CH_2)_m\text{—}CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1\text{-}C_8$alkyl, $C_2\text{-}C_8$alkenyl, $C_2\text{-}C_8$alkynyl, aryl, glucosyl, wherein the 5 or 6-membered lactone, $C_1\text{-}C_8$alkyl, $C_2\text{-}C_8$alkenyl, $C_2\text{-}C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1\text{-}C_8$ alkyl, $C_2\text{-}C_8$ alkenyl, $C_2\text{-}C_8$ alkynyl, $C_3\text{-}C_8$ cycloalkyl, and $C_1\text{-}C_8$ haloalkyl;

each of $R_5$ and $R_6$ is independently a hydrogen or $C_1\text{-}C_8$alkyl;

$R_7$ is a $C_1\text{-}C_8$alkyl, $OR_5$ or $NR_5R_6$;

m=1-12; and n=1-12; or a pharmaceutically acceptable salt, metabolite, solvate or prodrug thereof.

In some embodiments, the vasculature comprises a cardiac artery. In certain embodiments, the vasculature comprises an aorta. In some embodiments, the subject is human.

In some embodiments, the cyclohexenone compounds provided herein possess the therapeutic effects of inhibiting the production or progression of atherosclerotic lesions. See Example 8.

In some embodiments provide methods for preventing or treating an inflammation-related arteriosclerotic vascular disease in a subject comprising administering to the subject a therapeutically effective amount of a cyclohexenone compound having the structure:

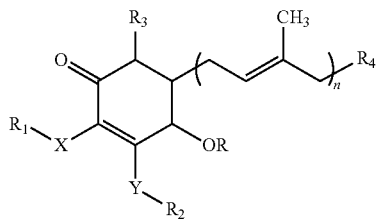

wherein each of X and Y independently is oxygen, $NR_5$ or sulfur;

R is a hydrogen or $C(=O)C_1\text{-}C_8$alkyl;

each of $R_1$, $R_2$ and $R_3$ independently is a hydrogen, methyl or $(CH_2)_m\text{—}CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1\text{-}C_8$alkyl, $C_2\text{-}C_8$alkenyl, $C_2\text{-}C_8$alkynyl, aryl, glucosyl, wherein the 5 or 6-membered lactone, $C_1\text{-}C_8$alkyl, $C_2\text{-}C_8$alkenyl, $C_2\text{-}C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1\text{-}C_8$ alkyl, $C_2\text{-}C_8$ alkenyl, $C_2\text{-}C_8$ alkynyl, $C_3\text{-}C_8$ cycloalkyl, and $C_1\text{-}C_8$ haloalkyl;

each of $R_5$ and $R_6$ is independently a hydrogen or $C_1\text{-}C_8$alkyl;

$R_7$ is a $C_1\text{-}C_8$alkyl, $OR_5$ or $NR_5R_6$;

m=1-12; and n=1-12; or a pharmaceutically acceptable salt, metabolite, solvate or prodrug thereof. In some embodiments, the subject is human.

In some embodiments provide methods reducing C-reactive protein in a subject comprising administering to the subject a therapeutically effective amount of a cyclohexenone compound having the structure:

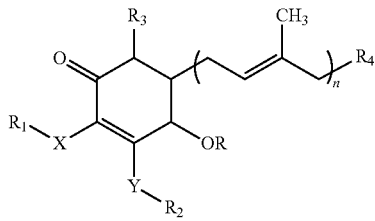

wherein each of X and Y independently is oxygen, $NR_5$ or sulfur;
R is a hydrogen or $C(=O)C_1-C_8$alkyl;
each of $R_1$, $R_2$ and $R_3$ independently is a hydrogen, methyl or $(CH_2)_m—CH_3$;
$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1-C_8$alkyl, $C_2-C_8$alkenyl, $C_2-C_8$alkynyl, aryl, glucosyl, wherein the 5 or 6-membered lactone, $C_1-C_8$alkyl, $C_2-C_8$alkenyl, $C_2-C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1-C_8$ alkyl, $C_2-C_8$ alkenyl, $C_2-C_8$ alkynyl, $C_3-C_8$ cycloalkyl, and $C_1-C_8$ haloalkyl;
each of $R_5$ and $R_6$ is independently a hydrogen or $C_1-C_8$alkyl;
$R_7$ is a $C_1-C_8$alkyl, $OR_5$ or $NR_5R_6$;
m=1-12; and
n=1-12; or a pharmaceutically acceptable salt, metabolite, solvate or prodrug thereof.

In some embodiments, the subject is human.

C-reactive protein (CRP) is a protein found in the blood, the levels of which rise in response to inflammation (i.e. C-reactive protein is an acute-phase protein). Its physiological role is to bind to phosphocholine expressed on the surface of dead or dying cells (and some types of bacteria) in order to activate the complement system via the C1Q complex.

According to the lipid hypothesis, abnormal cholesterol levels (hypercholesterolemia)—that is, higher concentrations of LDL and lower concentrations of functional HDL—are strongly associated with cardiovascular disease because these promote atheroma development in arteries (atherosclerosis). This disease process leads to myocardial infarction (heart attack), stroke, and peripheral vascular disease. Since higher blood LDL, especially higher LDL particle concentrations and smaller LDL particle size, contribute to this process more than the cholesterol content of the HDL particles, LDL particles (cholesterol) are often termed "bad cholesterol" because they have been linked to atheroma formation.

Elevated levels of the lipoprotein fractions, LDL, IDL and VLDL are regarded as atherogenic (prone to cause atherosclerosis). Levels of these fractions, rather than the total cholesterol level, correlate with the extent and progress of atherosclerosis. Conversely, the total cholesterol can be within normal limits, yet be made up primarily of small LDL and small HDL particles, under which conditions atheroma growth rates would still be high. In contrast, however, if LDL particle (LDL cholesterol or LDL-c) number is low (mostly large particles) and a large percentage of the HDL particles are large, then atheroma growth rates are usually low, even negative, for any given total cholesterol concentration.

The desirable LDL-c level is considered to be less than 100 mg/dL (2.6 mmol/L), although a newer upper limit of 70 mg/dL (1.8 mmol/L) can be considered in higher-risk individuals based on some of the above-mentioned trials. A ratio of total cholesterol to HDL—another useful measure—of far less than 5:1 is thought to be healthier.

The low-density lipoprotein (LDL) receptor (LDLR) is the primary pathway for removal of cholesterol from the circulation (Slater H R, et al., Thrombosis, and Vascular Biology 1984; 4(6):604-13). Expression of the LDLR on the liver cell surface regulates homeostasis of human blood LDL cholesterol (LDL-c). Increased hepatic LDLR expression improves the clearance of blood LDL-c through a receptor mediated endocytosis (Brown M S, et al., Science 1986 Apr. 4; 232(4746):34-47; Goldstein J L, et al., Nature 1990; 343(6257):425-30). LDLR-mediated hepatic up-take is considered to be responsible for the removal of more than 70% of human LDL-c (Brown M S, et al., Science 1986 Apr. 4; 232(4746):34-47).

In some embodiments, provided herein are methods lowering low-density lipoprotein (LDL) cholesterol or maintaining a normal LDL cholesterol level in a subject by administering a cyclohexenone compound provided herein to the subject (e.g. a human). The cyclohexenone compounds provide therapeutic benefit to a subject being treated for lowering LDL cholesterol to normal range (see Examples 1, 10-14). The invention cyclohexenone compounds, in some embodiments, are obtained from extracts of natural products and provide reduced complications and/or side effects. In some embodiments, this invention provides the therapeutic and prophylactic potential of exemplary cyclohexenone compounds (e.g., Compound 1) for lowering LDL cholesterol or maintaining normal LDL cholesterol level by inducing LDL receptor.

In some embodiments, the present invention provides results indicating that the expression of LDLR mRNA is activated by exemplary cyclohexenone compounds (e.g., Compound 1, at a concentration of 2004). The level of LDLR mRNA expression was increase as early as 2 h after the addition to the cells of Compound 1. The increase reached a significant level at 4 h and continuously increased up to 6 h at the end of the experiment (see Example 10, FIGS. 10A and 10B). It has been shown that extracellular signal-regulated kinase (ERK1/2) activation is positively correlated with the LDLR mRNA stabilization in hepatoma cells (Abidi P, Zhou Y, et al., Thrombosis, and Vascular Biology 2005; 25(10):2170-6; Kong W, et al. Nat Med 2004; 10(12):1344-51).

In some embodiments, based on the immunoblotting results, lower concentration level of the exemplary cyclohexenone compounds (e.g., Compound 1 at 0.5 μM) was enough to induce the activation of ERK1/2 in the HepG2 (See Example 11, FIGS. 11A and 11B). In certain embodiments, the exemplary cyclohexenone compounds (e.g., Compound 1) elevate LDLR mRNA expression through ERK-dependent pathway in human hepatoma cells.

In some embodiments, there are provided methods of lowering low-density lipoprotein (LDL) cholesterol or maintaining a normal LDL cholesterol level in a subject comprising administering to the subject a therapeutically effective amount of a cyclohexenone compound having the structure:

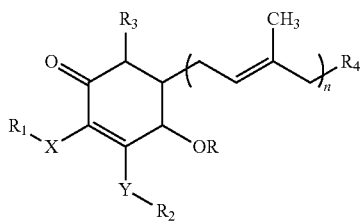

wherein each of X and Y independently is oxygen, $NR_5$ or sulfur;

R is a hydrogen or $C(=O)C_1-C_8$alkyl;

each of $R_1$, $R_2$ and $R_3$ independently is a hydrogen, methyl or $(CH_2)_m-CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1-C_8$alkyl, $C_2-C_8$alkenyl, $C_2-C_8$alkynyl, aryl, glucosyl, wherein the 5 or 6-membered lactone, $C_1-C_8$alkyl, $C_2-C_8$alkenyl, $C_2-C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1-C_8$ alkyl, $C_2-C_8$ alkenyl, $C_2-C_8$ alkynyl, $C_3-C_8$ cycloalkyl, and $C_1-C_8$ haloalkyl;

each of $R_5$ and $R_6$ is independently a hydrogen or $C_1-C_8$alkyl;

$R_7$ is a $C_1-C_8$alkyl, $OR_5$ or $NR_5R_6$;

m=1-12; and n=1-12; or a pharmaceutically acceptable salt, metabolite, solvate or prodrug thereof.

In some embodiments, the compound induces low-density lipoprotein (LDL) receptor expression in the subject. In some embodiments, the compound increases hepatic LDLR expression. In some embodiments, the method induces low-density lipoprotein (LDL) receptor expression in the subject. In some embodiments, the method increases hepatic LDLR expression. In some embodiments, the subject is human. In certain embodiments, the methods reduce or maintain LDL cholesterol to a level less than 100 mg/dL (2.6 mmol/L) in human. See Examples 10-14.

In some embodiments, the cyclohexenone compound having the structure

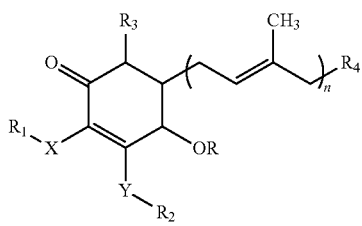

is prepared synthetically or semi-synthetically from any suitable starting material. In other embodiments, the cyclohexenone compound is prepared by fermentation, or the like. For example, Compound 1 (also known as Antroquinonol™ or "Antroq") or Compound 3, in some instances, is prepared from 4-hydroxy-2,3-dimethoxy-6-methylcyclohexa-2,5-dienone. The non-limited exemplary compounds are illustrated below.

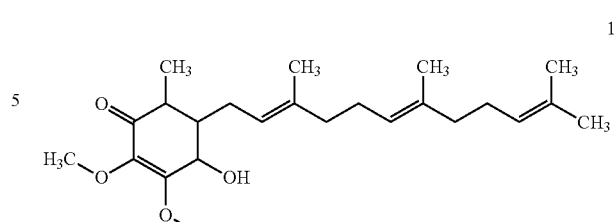

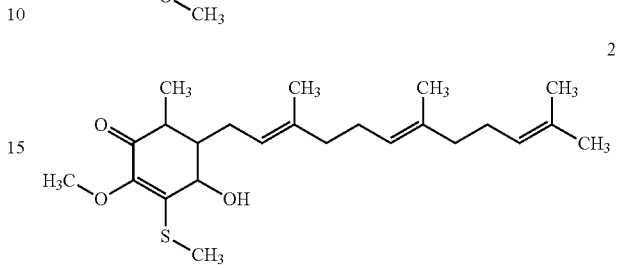

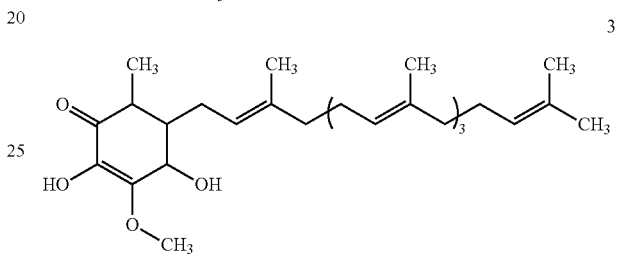

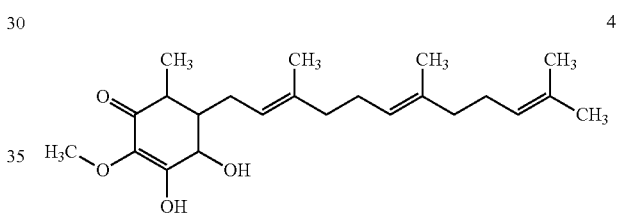

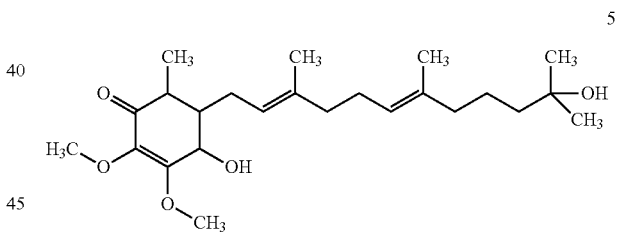

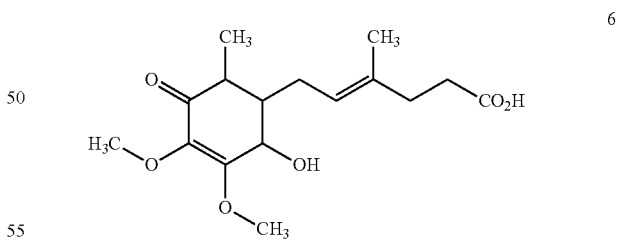

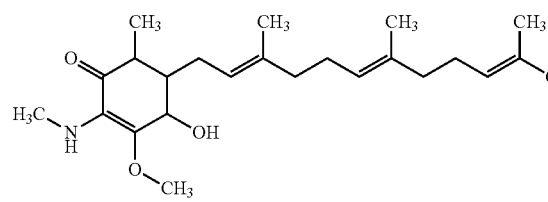
8
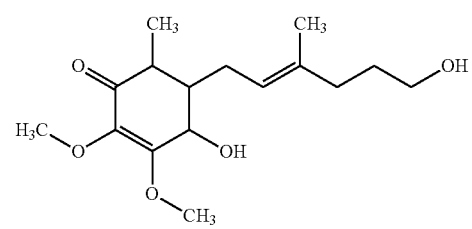
9
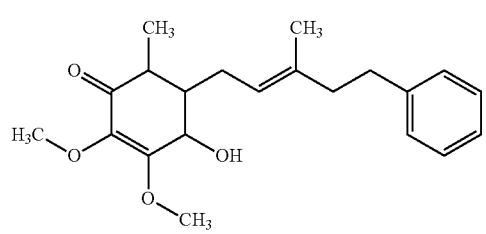
10
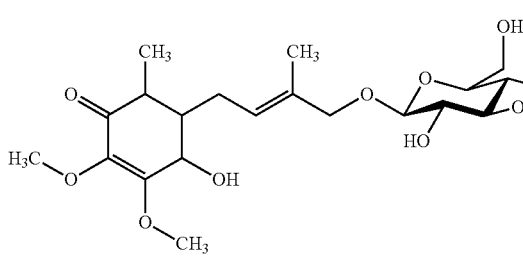
11
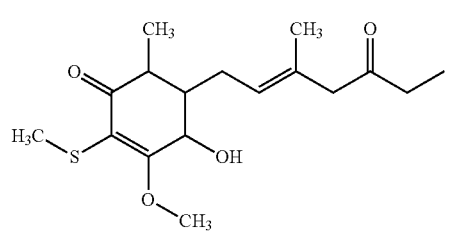
12
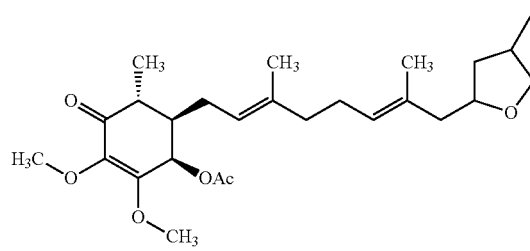
13
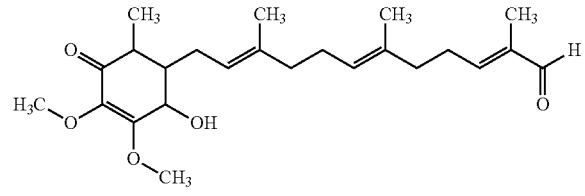
14
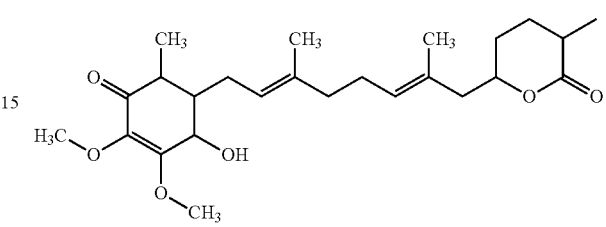
15
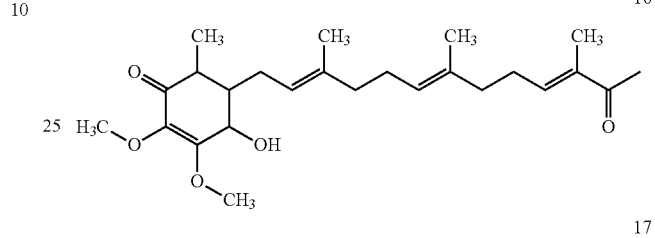
16
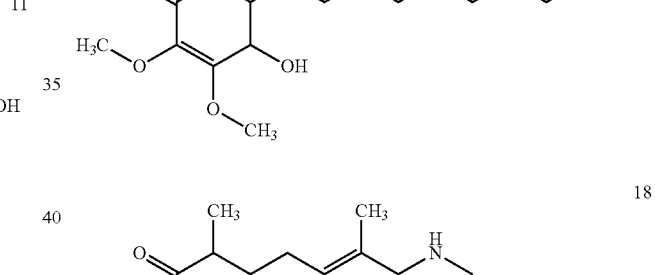
17
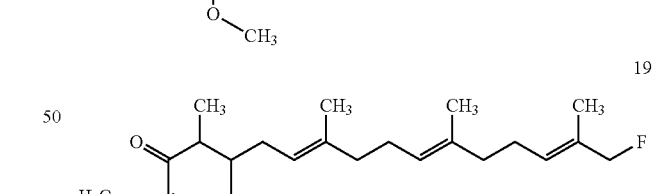
18
19
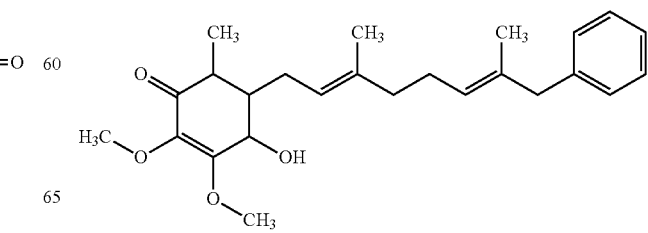
20

In other embodiments, the cyclohexenone compound having the structure

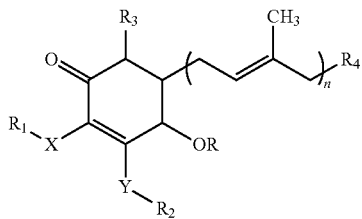

is isolated from the organic solvent extracts of *Antrodia camphorata*. In some embodiments, the organic solvent is selected from alcohols (e.g., methanol, ethanol, propanol, or the like), esters (e.g., methyl acetate, ethyl acetate, or the like), alkanes (e.g., pentane, hexane, heptane, or the like), halogenated alkanes (e.g., chloromethane, chloroethane, chloroform, methylene chloride, and the like), and the like. For example, exemplary Compounds 1-7 are isolated from organic solvent extracts. In certain embodiments, the organic solvent is alcohol. In certain embodiments, the alcohol is ethanol. In some embodiments, the cyclohexenone compound is isolated from the aqueous extracts of *Antrodia camphorata*.

In some embodiments, R is a hydrogen, $C(=O)C_3H_8$, $C(=O)C_2H_5$, or $C(=O)CH_3$. In some embodiments, $R_1$ is a hydrogen or methyl. In certain embodiments, $R_2$ is a hydrogen, methyl, ethyl, propyl, butyl, pentyl or hexyl. In some embodiments, $R_3$ is a hydrogen, methyl, ethyl, propyl, butyl, pentyl or hexyl. In some embodiments, $R_4$ is halogen, $NH_2$, $NHCH_3$, $N(CH_3)_2$, $OCH_3$, $OC_2H_5$, $C(=O)CH_3$, $C(=O)C_2H_5$, $C(=O)OCH_3$, $C(=O)OC_2H_5$, $C(=O)NHCH_3$, $C(=O)NHC_2H_5$, $C(=O)NH_2$, $OC(=O)CH_3$, $OC(=O)C_2H_5$, $OC(=O)OCH_3$, $OC(=O)OC_2H_5$, $OC(=O)NHCH_3$, $OC(=O)NHC_2H_5$, or $OC(=O)NH_2$. In some embodiments, $R_4$ is $C_2H_5C(CH_3)_2OH$, $C_2H_5C(CH_3)_2OCH_3$, $CH_2COOH$, $C_2H_5COOH$, $CH_2OH$, $C_2H_5OH$, $CH_2Ph$, $C_2H_5Ph$, $CH_2CH=C(CH_3)(CHO)$, $CH_2CH=C(CH_3)(C(=O)CH_3)$, 5 or 6-membered lactone, $C_1$-$C_8$alkyl, $C_2$-$C_8$alkenyl, $C_2$-$C_8$alkynyl, aryl, and glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl. In certain embodiments, $R_4$ is $CH_2CH=C(CH_3)_2$. In certain embodiments, the compound is

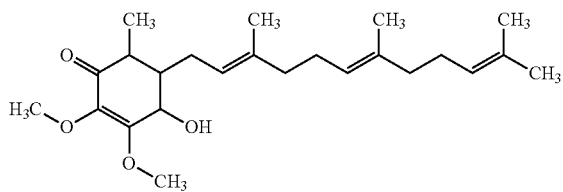

Certain Pharmaceutical and Medical Terminology

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described.

An "alkyl" group refers to an aliphatic hydrocarbon group. The alkyl group may be a saturated alkyl group (which means that it does not contain any carbon-carbon double bonds or carbon-carbon triple bonds) or the alkyl group may be an unsaturated alkyl group (which means that it contains at least one carbon-carbon double bonds or carbon-carbon triple bond). The alkyl moiety, whether saturated or unsaturated, may be branched, or straight chain.

The "alkyl" group may have 1 to 12 carbon atoms (whenever it appears herein, a numerical range such as "1 to 12 refers to each integer in the given range; e.g., "1 to 12 carbon atoms" means that the alkyl group may consist of 1 carbon atom, 2 carbon atoms, 3 carbon atoms, etc., up to and including 12 carbon atoms, although the present definition also covers the occurrence of the term "alkyl" where no numerical range is designated). The alkyl group of the compounds described herein may be designated as "$C_1$-$C_8$ alkyl" or similar designations. By way of example only, "$C_1$-$C_8$ alkyl" indicates that there are one, two, three, four, five, six, seven or eight carbon atoms in the alkyl chain. In one aspect the alkyl is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, sec-butyl, tertiary butyl, pentyl, neopentyl, hexyl, allyl, but-2-enyl, but-3-enyl, cyclopropylmethyl, cyclobutylmethyl, cyclopentylmethyl, cyclohexylmethyl, and the like. In one aspect, an alkyl is a $C_1$-$C_8$ alkyl.

The term "alkylene" refers to a divalent alkyl radical. Any of the above mentioned monovalent alkyl groups may be an alkylene by abstraction of a second hydrogen atom from the alkyl. In one aspect, an alkylene is a $C_1$-$C_{12}$alkylene. In another aspect, an alkylene is a $C_1$-$C_8$alkylene. Typical alkylene groups include, but are not limited to, —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, —$CH_2CH_2CH_2CH_2$—, and the like.

As used herein, the term "aryl" refers to an aromatic ring wherein each of the atoms forming the ring is a carbon atom. Aryl rings are formed by five, six, seven, eight, nine, or more than nine carbon atoms. Aryl groups are optionally substituted. In one aspect, an aryl is a phenyl or a naphthalenyl. In one aspect, an aryl is a phenyl. In one aspect, an aryl is a $C_6$-$C_{10}$aryl. Depending on the structure, an aryl group can be a monoradical or a diradical (i.e., an arylene group). In one aspect, an arylene is a $C_6$-$C_{10}$ arylene. Exemplary arylenes include, but are not limited to, phenyl-1,2-ene, phenyl-1,3-ene, and phenyl-1,4-ene.

The term "aromatic" refers to a planar ring having a delocalized π-electron system containing 4n+2π electrons, where n is an integer. Aromatic rings can be formed from five, six, seven, eight, nine, ten, or more than ten atoms. Aromatics are optionally substituted. The term "aromatic" includes both carbocyclic aryl ("aryl", e.g., phenyl) and heterocyclic aryl (or "heteroaryl" or "heteroaromatic")

groups (e.g., pyridine). The term includes monocyclic or fused-ring polycyclic (i.e., rings which share adjacent pairs of carbon atoms) groups.

The term "halo" or, alternatively, "halogen" or "halide" means fluoro, chloro, bromo or iodo.

The term "lactone" refers to a cyclic ester which can be seen as the condensation product of an alcohol group —OH and a carboxylic acid group —COOH in the same molecule. It is characterized by a closed ring consisting of two or more carbon atoms and a single oxygen atom, with a ketone group =O in one of the carbons adjacent to the other oxygen.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 4 to 10 atoms in its ring system, and with the proviso that the any ring does not contain two adjacent O or S atoms. Non-aromatic heterocyclic groups (also known as heterocycloalkyls) include groups having only 3 atoms in their ring system, but aromatic heterocyclic groups must have at least 5 atoms in their ring system. The heterocyclic groups include benzo-fused ring systems. An example of a 3-membered heterocyclic group is aziridinyl. An example of a 4-membered heterocyclic group is azetidinyl. An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups may be C-attached or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles may be substituted with one or two oxo (=O) moieties, such as pyrrolidin-2-one.

The term "alkenyl" as used herein, means a straight, branched chain, or cyclic (in which case, it would also be known as a "cycloalkenyl") hydrocarbon containing from 2-10 carbons and containing at least one carbon-carbon double bond formed by the removal of two hydrogens. In some embodiments, depending on the structure, an alkenyl group is a monoradical or a diradical (i.e., an alkenylene group). In some embodiments, alkenyl groups are optionally substituted. Illustrative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-cecenyl.

The term "alkynyl" as used herein, means a straight, branched chain, or cyclic (in which case, it would also be known as a "cycloalkenyl") hydrocarbon containing from 2-10 carbons and containing at least one carbon-carbon triple bond formed by the removal of four hydrogens. In some embodiments, depending on the structure, an alkynyl group is a monoradical or a diradical (i.e., an alkynylene group). In some embodiments, alkynyl groups are optionally substituted. Illustrative examples of alkynyl include, but are not limited to, ethynyl, propynyl, butyryl, pentynyl, hexynyl, heptynyl, and the like.

The term "alkoxy" as used herein, means an alkyl group, as defined herein, appended to the parent molecular moiety through an oxygen atom. Illustrative examples of alkoxy include, but are not limited to, methoxy, ethoxy, propoxy, 2-propoxy, butoxy, tert-butoxy, pentyloxy, and hexyloxy.

The term "cycloalkyl" as used herein, means a monocyclic or polycyclic radical that contains only carbon and hydrogen, and includes those that are saturated, partially unsaturated, or fully unsaturated. Cycloalkyl groups include groups having from 3 to 10 ring atoms. Representative examples of cyclic include but are not limited to, the following moieties:

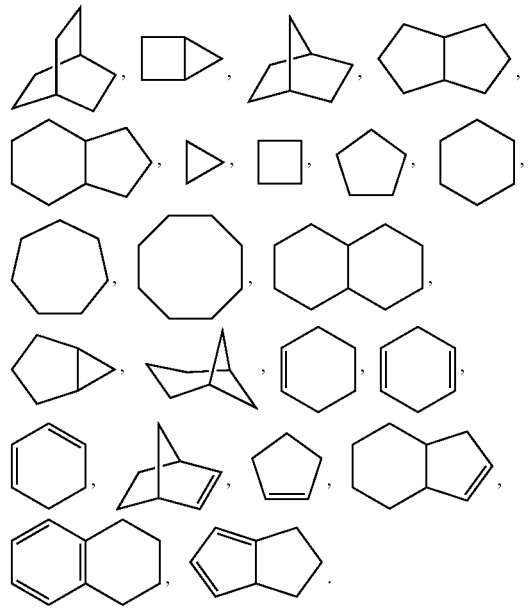

In some embodiments, depending on the structure, a cycloalkyl group is a monoradical or a diradical (e.g., a cycloalkylene group).

The terms "haloalkyl," "haloalkenyl," "haloalkynyl" and "haloalkoxy" as used herein, include alkyl, alkenyl, alkynyl and alkoxy structures in which at least one hydrogen is replaced with a halogen atom. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another. The terms "fluoroalkyl" and "fluoroalkoxy" include haloalkyl and haloalkoxy groups, respectively, in which the halo is fluorine. In certain embodiments, haloalkyls are optionally substituted.

The term "glucosyl" as used herein, include D- or L-form glucosyl groups, in which the glucosyl group is attached via any hydroxyl group on the glucose ring.

The term "acceptable" with respect to a formulation, composition or ingredient, as used herein, means having no persistent detrimental effect on the general health of the subject being treated.

*Antrodia* is a genus of fungi in the family Meripilaceae. *Antrodia* species have fruiting bodies that typically lie flat or spread out on the growing surface, with the hymenium exposed to the outside; the edges may be turned so as to form narrow brackets. Most species are found in temperate and boreal forests, and cause brown rot. Some of the species in this genus are have medicinal properties, and have been used in Taiwan as a Traditional medicine.

The term "carrier," as used herein, refers to relatively nontoxic chemical compounds or agents that facilitate the incorporation of a compound into cells or tissues.

The terms "co-administration" or the like, as used herein, are meant to encompass administration of the selected therapeutic agents to a single patient, and are intended to include treatment regimens in which the agents are administered by the same or different route of administration or at the same or different time.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound (i.e., a cyclohexenone compound described herein) and a co-agent, are both administered to a patient simultaneously in the form of a single entity or dosage. The term "non-fixed combination" means that the active ingredients, e.g. a compound (i.e., a cyclohexenone compound described herein) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of a compound (i.e., a cyclohexenone compound described herein) with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

In some embodiments, the cyclohexenone compound, or a pharmaceutically acceptable salt, metabolite, solvate or prodrug thereof, is administered parenterally or intravenously. In other embodiments, the cyclohexenone compound, or a pharmaceutically acceptable salt, metabolite, solvate or prodrug thereof, is administered by injection. In some embodiments, the cyclohexenone compound, or a pharmaceutically acceptable salt, metabolite, solvate or prodrug thereof, is administered orally.

Pharmaceutical Composition/Formulation

In some embodiments provide pharmaceutical compositions comprising a therapeutically effective amount of a cyclohexenone compound having the structure:

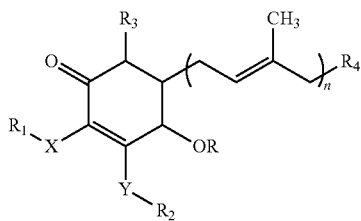

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof. In some embodiments, the compositions further comprise a pharmaceutically acceptable excipient.

In some embodiments, R is a hydrogen, $C(=O)C_3H_8$, $C(=O)C_2H_5$, or $C(=O)CH_3$. In some embodiments, each of $R_1$, $R_2$ and $R_3$ independently is a hydrogen, methyl, ethyl, propyl, butyl, pentyl hexyl, heptyl, or octyl. In certain embodiments, $R_1$ is a hydrogen or methyl. In certain embodiments, $R_2$ is a hydrogen, methyl, ethyl, propyl, butyl, pentyl or hexyl. In certain embodiments, $R_3$ is a hydrogen, methyl, ethyl, propyl, butyl, pentyl or hexyl. In some embodiments, $R_4$ is halogen, $NH_2$, $NHCH_3$, $N(CH_3)_2$, $OCH_3$, $OC_2H_5$, $C(=O)CH_3$, $C(=O)C_2H_5$, $C(=O)OCH_3$, $C(=O)OC_2H_5$, $C(=O)NHCH_3$, $C(=O)NHC_2H_5$, $C(=O)NH_2$, $OC(=O)CH_3$, $OC(=O)C_2H_5$, $OC(=O)OCH_3$, $OC(=O)OC_2H_5$, $OC(=O)NHCH_3$, $OC(=O)NHC_2H_5$, or $OC(=O)NH_2$. In certain embodiments, $R_4$ is $C_2H_5$ $C(CH_3)_2OH$, $C_2H_5C(CH_3)_2OCH_3$, $CH_2COOH$, $C_2H_5COOH$, $CH_2OH$, $C_2H_5OH$, $CH_2Ph$, $C_2H_5Ph$, $CH_2CH=C(CH_3)(CHO)$, $CH_2CH=C(CH_3)(C(=O)CH_3)$, 5 or 6-membered lactone, aryl, or glucosyl, wherein 5 or 6-membered lactone, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl. In certain embodiments, $R_4$ is $CH_2COOH$, $C_2H_5COOH$, $CH_2OH$, $C_2H_5OH$, $CH_2Ph$, $C_2H_5Ph$, $CH_2CH=C(CH_3)(CHO)$, $CH_2CH=C(CH_3)(C(=O)CH_3)$, 5 or 6-membered lactone, aryl, or glucosyl, wherein the 5 or 6-membered lactone, $C_1$-$C_8$alkyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl.

In certain embodiments, the compound is selected from group consisting of

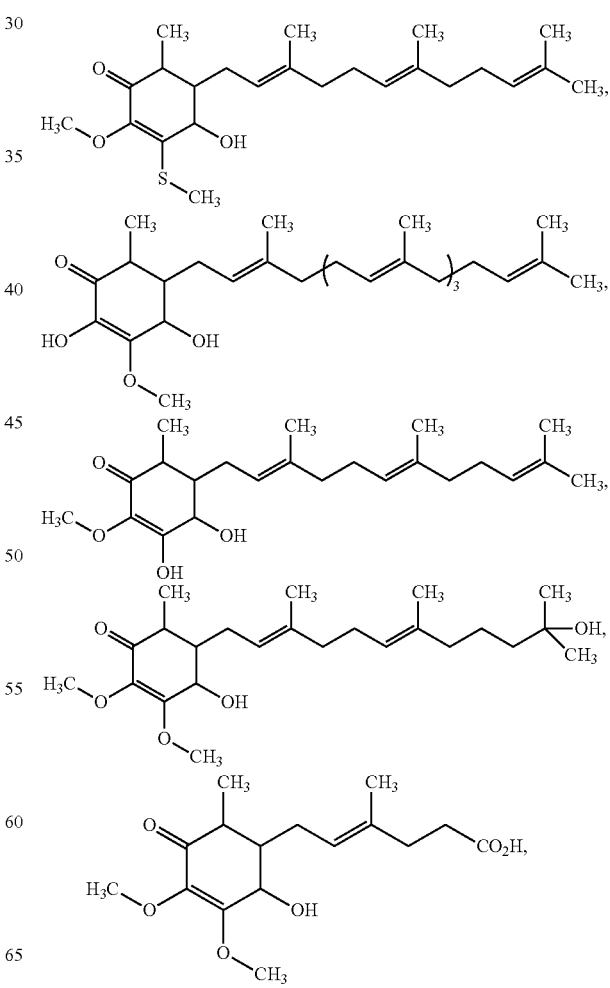

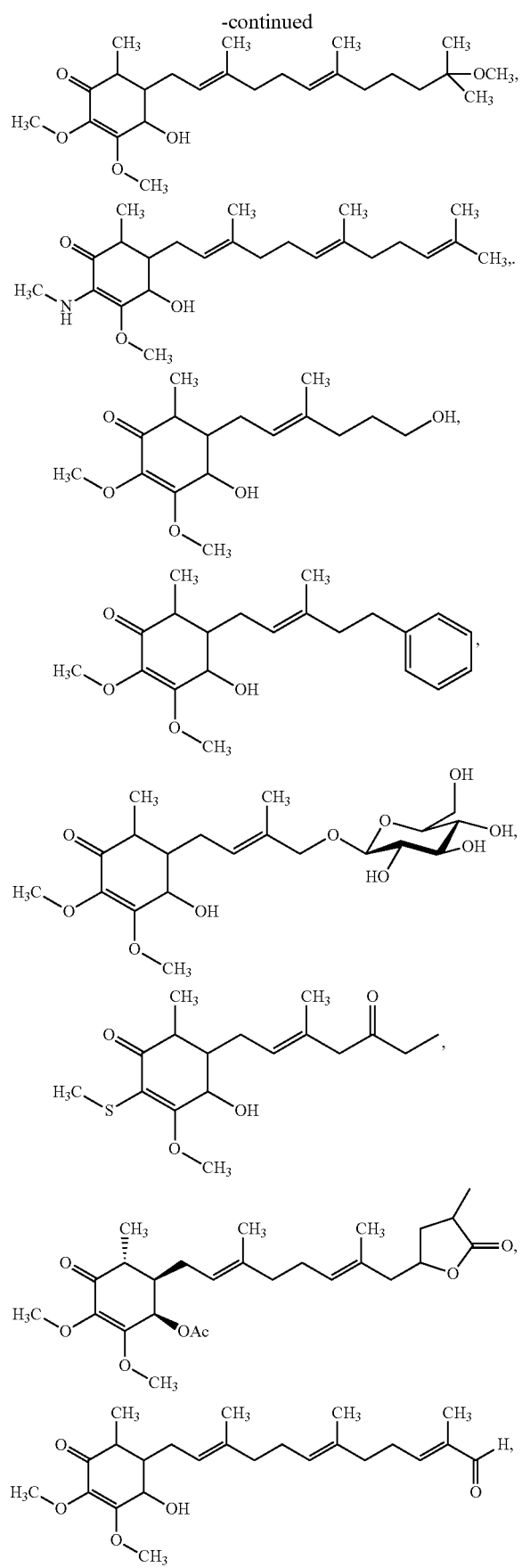
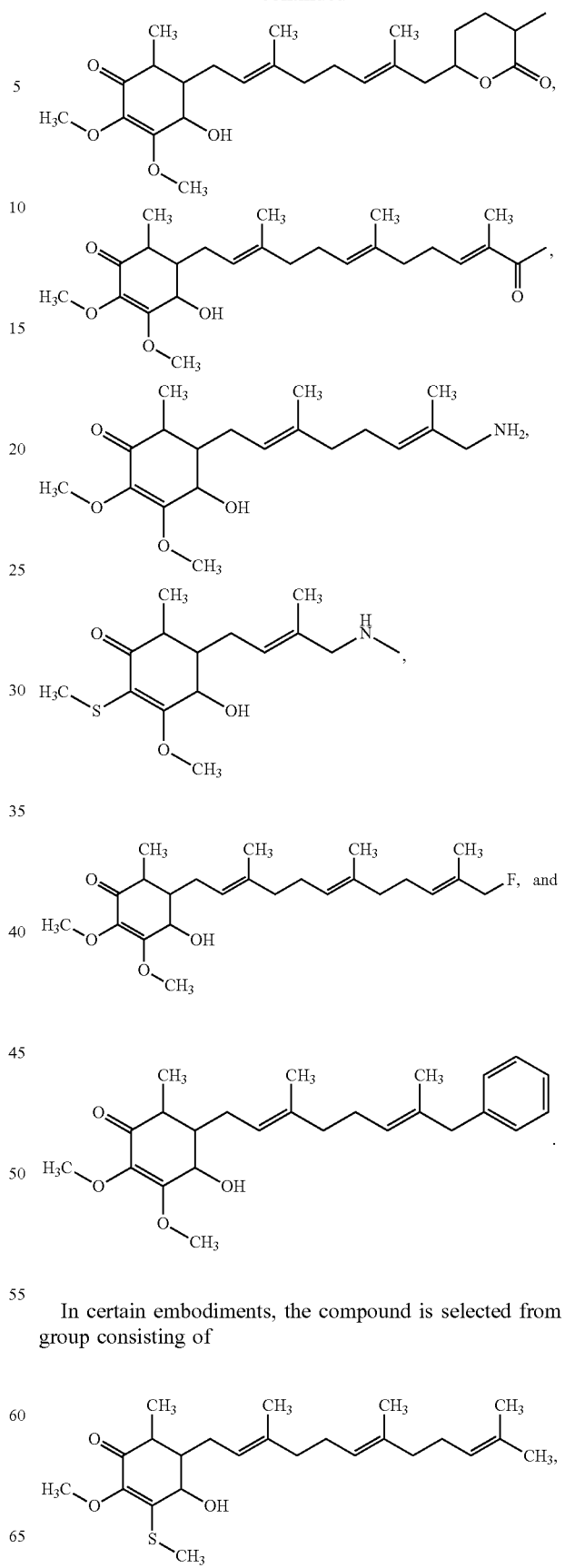
In certain embodiments, the compound is selected from group consisting of

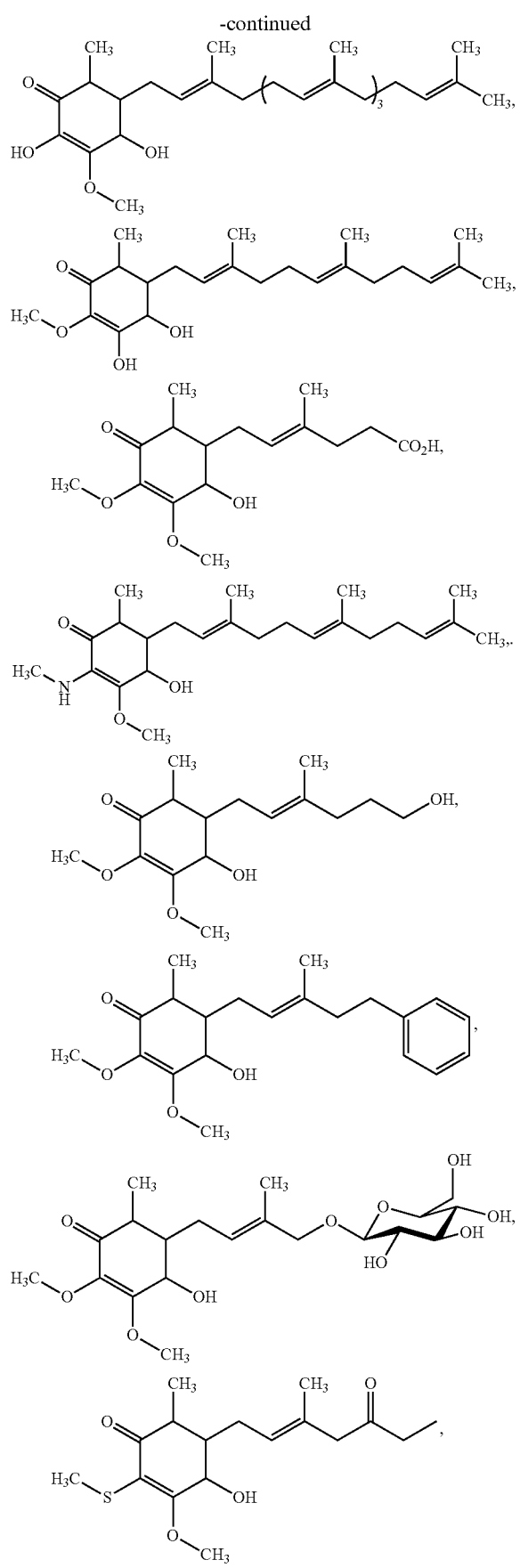
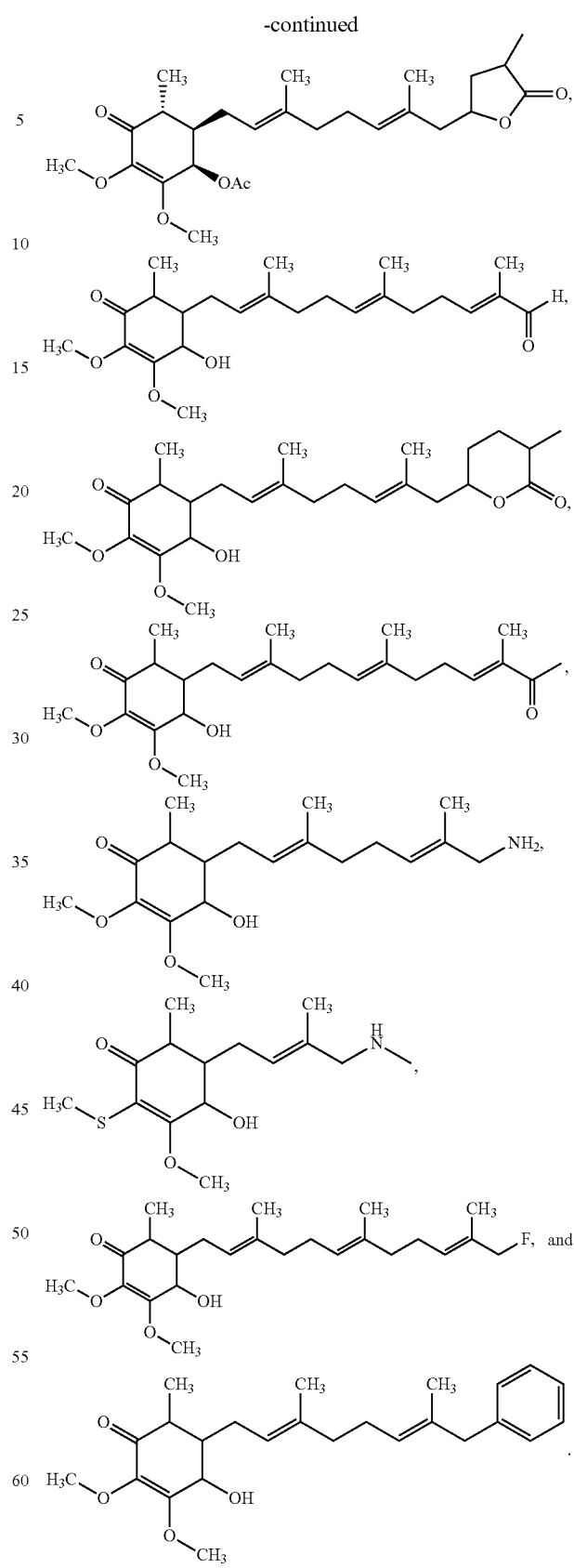
In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

Provided herein are pharmaceutical compositions comprising a compound (i.e., a cyclohexenone compound described herein) and a pharmaceutically acceptable diluent(s), excipient(s), or carrier(s). In certain embodiments, the compounds described are administered as pharmaceutical compositions in which a compound (i.e., a cyclohexenone compound described herein) is mixed with other active ingredients, as in combination therapy. Encompassed herein are all combinations of actives set forth in the combination therapies section below and throughout this disclosure. In specific embodiments, the pharmaceutical compositions include one or more compounds (i.e., a cyclohexenone compound described herein).

A pharmaceutical composition, as used herein, refers to a mixture of a compound (i.e., a cyclohexenone compound described herein) with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds (i.e., a cyclohexenone compound described herein) are administered in a pharmaceutical composition to a mammal having a disease or condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, a compound (i.e., a cyclohexenone compound described herein) is formulated in an aqueous solution. In specific embodiments, the aqueous solution is selected from, by way of example only, a physiologically compatible buffer, such as Hank's solution, Ringer's solution, or physiological saline buffer. In other embodiments, a compound (i.e., a cyclohexenone compound described herein) is formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or nonaqueous solutions. In specific embodiments, such solutions include physiologically compatible buffers and/or excipients.

In another embodiment, compounds described herein are formulated for oral administration. Compounds described herein, including a compound (i.e., a cyclohexenone compound described herein), are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipients with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds described herein are formulated for buccal or sublingual administration. Formulations suitable for buccal or sublingual administration include, by way of example only, tablets, lozenges, or gels. In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions of a compound (i.e., a cyclohexenone compound described herein) are formulated in a form suitable for parenteral injection as a sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In one aspect, compounds (i.e., cyclohexenone compounds described herein) are prepared as solutions for parenteral injection as described herein or known in the art and administered with an automatic injector. Automatic injectors, such as those disclosed in U.S. Pat. Nos. 4,031,893, 5,358,489; 5,540,664; 5,665,071, 5,695,472 and WO/2005/087297 (each of which are incorporated herein by reference for such disclosure) are known. In general, all automatic injectors contain a volume of solution that includes a compound (i.e., a cyclohexenone compound described herein) to be injected. In general, automatic injectors include a reservoir for holding the solution, which is in fluid communication with a needle for delivering the drug, as well as a mechanism for automatically deploying the needle, inserting the needle into the patient and delivering the dose into the patient. Exemplary injectors provide about 0.3 mL, 0.6 mL, 1.0 mL or other suitable volume of solution at about a concentration of 0.5 mg to 50 mg of a compound (i.e., a cyclohexenone compound described herein) per 1 mL of solution. Each injector is capable of delivering only one dose of the compound.

In still other embodiments, the compounds (i.e., cyclohexenone compounds described herein) are administered topically. The compounds described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the compounds (i.e., cyclohexenone compounds described herein) are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of a compound (i.e., cyclohexenone compound described herein) is accomplished by means of iontophoretic patches and the like. In certain embodiments, transdermal patches provide controlled delivery of a compound (i.e., a cyclohexenone compound described herein). In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Transdermal formulations described herein may be administered using a variety of devices which have been described in the art. For example, such devices include, but are not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144.

The transdermal dosage forms described herein may incorporate certain pharmaceutically acceptable excipients which are conventional in the art. In one embodiment, the transdermal formulations described herein include at least three components: (1) a formulation of a compound (i.e., a cyclohexenone compound described herein); (2) a penetration enhancer; and (3) an aqueous adjuvant. In addition, transdermal formulations can include additional components such as, but not limited to, gelling agents, creams and ointment bases, and the like. In some embodiments, the transdermal formulations further include a woven or nonwoven backing material to enhance absorption and prevent the removal of the transdermal formulation from the skin. In other embodiments, the transdermal formulations described herein maintain a saturated or supersaturated state to promote diffusion into the skin.

In other embodiments, the compounds (i.e., cyclohexenone compounds described herein) are formulated for administration by inhalation. Various forms suitable for administration by inhalation include, but are not limited to, aerosols, mists or powders. Pharmaceutical compositions of a compound (i.e., a cyclohexenone compound described herein) are conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatins for use in an inhaler or insufflator are formulated containing a powder mix of the compound and a suitable powder base such as lactose or starch.

Intranasal formulations are known in the art and are described in, for example, U.S. Pat. Nos. 4,476,116, 5,116,817 and 6,391,452, each of which is specifically incorporated herein by reference. Formulations, which include a compound (i.e., a cyclohexenone compound described herein), which are prepared according to these and other techniques well-known in the art are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are found in sources such as REMINGTON: THE SCIENCE AND PRACTICE OF PHARMACY, 21st edition, 2005, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. Preferably, the nasal dosage form should be isotonic with nasal secretions.

For administration by inhalation, the compounds described herein, may be in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

In still other embodiments, the compounds (i.e., cyclohexenone compounds described herein) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients is optionally used as suitable and as understood in the art. Pharmaceutical compositions comprising a compound (i.e., a cyclohexenone compound described herein) may be manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one compound (i.e., cyclohexenone compounds described herein) described herein as an active ingredient. The active ingredient is in free-acid or free-base form, or in a pharmaceutically acceptable salt form. In addition, the methods and pharmaceutical compositions described herein include the use crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising at least compound (i.e., cyclohexenone compounds described herein) illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, pharmaceutical aqueous suspensions include one or more polymers as suspending agents. Polymers include water-soluble polymers such as cellulosic polymers, e.g., hydroxypropyl methylcellulose, and water-insoluble polymers such as cross-linked carboxyl-containing polymers. Certain pharmaceutical compositions described herein include a mucoadhesive polymer, selected from, for example, carboxymethylcellulose, carbomer (acrylic acid polymer), poly(methylmethacrylate), polyacrylamide, polycarbophil, acrylic acid/butyl acrylate copolymer, sodium alginate and dextran.

Pharmaceutical compositions also, optionally include solubilizing agents to aid in the solubility of a compound (i.e., cyclohexenone compounds described herein). The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, pharmaceutical compositions optionally include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other pharmaceutical compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other pharmaceutical compositions may include one or more antioxidants to enhance chemical stability where required. Suitable antioxidants include, by way of example only, ascorbic acid and sodium metabisulfite.

In certain embodiments, pharmaceutical aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few hours up to over 24 hours. Depending on the chemical nature and the biological stability of the therapeutic reagent, additional strategies for protein stabilization may be employed.

In certain embodiments, the formulations described herein include one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Combination Treatments

In general, the compositions described herein and, in embodiments where combinational therapy is employed, other agents do not have to be administered in the same pharmaceutical composition, and in some embodiments, because of different physical and chemical characteristics, are administered by different routes. In some embodiments, the initial administration is made according to established protocols, and then, based upon the observed effects, the dosage, modes of administration and times of administration is modified by the skilled clinician.

In some embodiments, therapeutically-effective dosages vary when the drugs are used in treatment combinations. Combination treatment further includes periodic treatments that start and stop at various times to assist with the clinical management of the patient. For combination therapies described herein, dosages of the co-administered compounds vary depending on the type of co-drug employed, on the specific drug employed, on the disease, disorder, or condition being treated and so forth.

It is understood that in some embodiments, the dosage regimen to treat, prevent, or ameliorate the condition(s) for which relief is sought, is modified in accordance with a variety of factors. These factors include the disorder from which the subject suffers, as well as the age, weight, sex, diet, and medical condition of the subject. Thus, in other embodiments, the dosage regimen actually employed varies widely and therefore deviates from the dosage regimens set forth herein.

Combinations of compounds (i.e., the cyclohexenone compound described herein) with other suitable agents for the treatment of atherosclerosis are intended to be covered. In some embodiments, examples of suitable agents for the treatment of atherosclerosis include, but are not limited to, the following: statins such as atorvastatin, fluvastatin, lovastatin, pitavastatin, pravastatin, rosuvastatin, simvastatin, combinations thereof, or the like; photosensitiser such as Motexafin lutetium; MK-0524A (niacin ER and laropiprant); anti-oxidatnts such as AC3056; anti-inflammatory agents such as steroids, non-steroidal anti-inflammatory drugs such as aspirin, ibuprofen, and naproxen or other COX-2 inhibitors, and the like; ACAT inhibitors such as Pactimibe, and the like; liver X receptor agonists such as Merck T0901317, and the like; or any derivative related agent of the foregoing.

The combinations of the cyclohexenone compounds and other suitable agents for the treatment of atherosclerosis described herein encompass additional therapies and treatment regimens with other agents in some embodiments. Such additional therapies and treatment regimens can include another agents for the treatment of atherosclerosis in some embodiments. Alternatively, in other embodiments, additional therapies and treatment regimens include other agents used to treat adjunct conditions associated with the atherosclerosis or a side effect from such agent in the combination therapy. In further embodiments, adjuvants or enhancers are administered with a combination therapy described herein.

Combinations of compounds (i.e., the cyclohexenone compound described herein) with other LDL cholesterol lowering agents (dietary supplements such as phytosterols, or therapeutic agents such as statins, ezetimibe, Niacin, clofibrate, or the like) are intended to be covered. In some embodiments, examples of LDL cholesterol lowering agents include statins. The combinations of the cyclohexenone compounds and other LDL cholesterol lowering agents described herein encompass additional therapies and treatment regimens with other agents in some embodiments. Such additional therapies and treatment regimens can include another LDL cholesterol lowering therapy in some embodiments. Alternatively, in other embodiments, additional therapies and treatment regimens include other agents used to treat adjunct conditions associated with the LDL cholesterol associated diseases or conditions or a side effect from such agent in the combination therapy. In further embodiments, adjuvants or enhancers are administered with a combination therapy described herein.

In some embodiments provide compositions for the treatment of atherosclerosis comprising a therapeutically effective amount of a cyclohexenone compound having the structure:

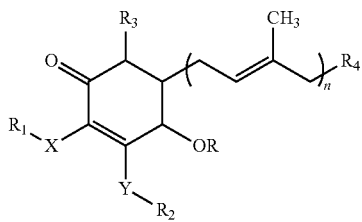

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof; and one or more LDL cholesterol lowering agents.

In some embodiments provide compositions for the treatment of atherosclerosis comprising a therapeutically effective amount of a cyclohexenone compound having the structure:

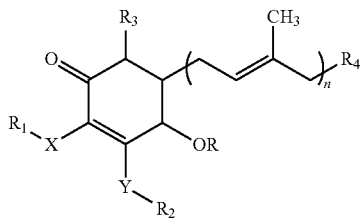

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently a hydrogen or $C_1$-$C_8$alkyl;

$R_7$ is a $C_1$-$C_8$alkyl, $OR_5$ or $NR_5R_6$;

m=1-12; and n=1-12; or a pharmaceutically acceptable salt, metabolite, solvate or prodrug thereof; and one or more statins.

EXAMPLES

Example 1

Preparation of the Exemplary Cyclohexenone Compounds

One hundred grams of mycelia, fruiting bodies or mixture of both from *Antrodia camphorata* were placed into a flask. A proper amount of water and alcohol (70-100% alcohol solution) was added into the flask and were stirred at 20-25° C. for at least 1 hour. The solution was filtered through a filter and 0.45 µm membrane and the filtrate was collected as the extract.

The filtrate of *Antrodia camphorata* was subjected to High Performance Liquid chromatography (HPLC) analysis. The separation was performed on a RP18 column, the mobile phase consisted of methanol (A) and 0.3% acetic acid (B), with the gradient conditions of 0-10 min in 95%-20% B, 10-20 min in 20%-10% B, 20-35 min in 10%-10% B, 35-40 min in 10%-95% B, at the flow rate of 1 ml/min. The column effluent was monitored with a UV-visible detector.

The fractions collected at 21.2 to 21.4 min were collected and concentrated to yield compound 5, a product of pale yellow liquid. Compound 5 was analyzed to be 4-hydroxy-5-(11-hydroxy-3,7,11-trimethyldodeca-2,6-dienyl)-2,3-dimethoxy-6-methylcyclohex-2-enone with molecular weight of 408 (Molecular formula: $C_{24}H_{40}O_5$). $^1$H-NMR (CDCl$_3$) δ(ppm)=1.21, 1.36, 1.67, 1.71, 1.75, 1.94, 2.03, 2.07, 2.22, 2.25, 3.68, 4.05, 5.71 and 5.56. $^{13}$C-NMR (CDCl$_3$) δ(ppm): 12.31, 16.1, 16.12, 17.67, 25.67, 26.44, 26.74, 27.00, 30.10, 40.27, 43.34, 59.22, 60.59, 71.8, 120.97, 123.84, 124.30, 131.32, 134.61, 135.92, 138.05, 160.45, and 197.11.

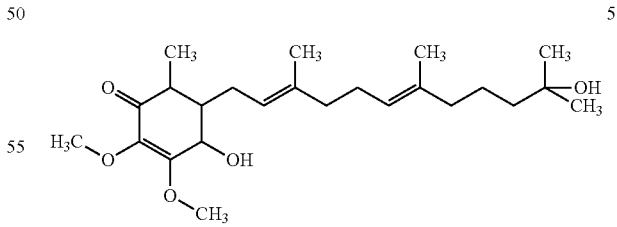

5

Compound 5: 4-hydroxy-5-(11-hydroxy-3,7,11-trimethyldodeca-2,6-dienyl)-2,3-dimethoxy-6-methylcyclohex-2-enone The fractions collected at 23.7 to 24.0 min were collected and concentrated to yield compound 7, a product of pale yellow liquid. Compound 7 was analyzed to be 4-hydroxy- 2,3-dimethoxy-5-(11-methoxy-3,7,11-trimethyldodeca-2,6-dienyl)-6-methylcyclohex-2-enone with molecular weight of 422 ($C_{25}H_{42}O_5$). $^1$H-NMR (CDCl$_3$) δ(ppm)=1.21, 1.36, 1.71, 1.75, 1.94, 2.03, 2.07, 2.22, 2.25, 3.24, 3.68, 4.05, 5.12, 5.50, and 5.61. $^{13}$C-NMR (CDCl$_3$) δ(ppm): 12.31, 16.1, 16.12, 17.67, 24.44, 26.44, 26.74, 27.00, 37.81, 39.81, 40.27, 43.34, 49.00, 59.22, 60.59, 120.97, 123.84, 124.30, 135.92, 138.05, 160.45 and 197.12.

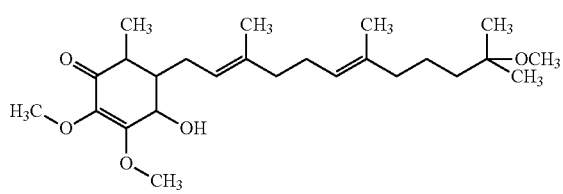

Compound 7: 4-hydroxy-2,3-dimethoxy-5-(11-methoxy-3,7,11-trimethyldodeca-2,6-dienyl)-6-methylcyclohex-2-enone The fractions collected at 25 to 30 min were collected and concentrated to yield 4-hydroxy-2,3-dimethoxy-6-methyl-5-(3,7,11-trimethyldodeca-2,6,10-trienyl)cyclohex-2-enone (compound 1), a product of pale yellow brown liquid. The analysis of compound 1 showed the molecular formula of $C_{24}H_{38}O_4$, molecular weight of 390 with melting point of 48 to 52° C. NMR spectra showed that $^1$H-NMR (CDCl$_3$) δ(ppm)=1.51, 1.67, 1.71, 1.75, 1.94, 2.03, 2.07, 2.22, 2.25, 3.68, 4.05, 5.07, and 5.14; $^{13}$C-NMR (CDCl$_3$) δ(ppm)=12.31, 16.1, 16.12, 17.67, 25.67, 26.44, 26.74, 27.00, 39.71, 39.81, 40.27, 43.34, 59.22, 60.59, 120.97, 123.84, 124.30, 131.32, 135.35, 135.92, 138.05, 160.45, and 197.12.

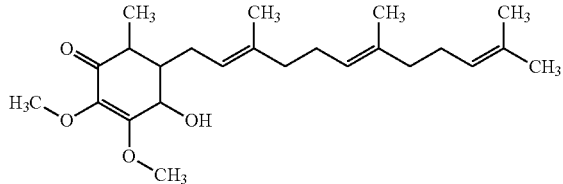 [SMILES: COC1=C(OC)C(O)C(C/C=C(\C)CC/C=C(\C)CCC=C(C)C)C(C)C1=O]

Compound 1: 4-hydroxy-2,3-dimethoxy-6-methyl-5-(3,7,11-trimethyldodeca-2,6,10-trienyl)cyclohex-2-enone Compound 6, a metabolite of compound 1, was obtained from urine samples of rats fed with Compound 1 in the animal study. Compound 6 was determined to be 4-hydroxy-2,3-dimethoxy-6-methyl-5-(3-methyl-2-hexenoic acid)cyclohex-2-enone with molecular weight of 312 ($C_{16}H_{24}O_6$). Compound 4 which was determined as 3,4-dihydroxy-2-methoxy-6-methyl-5-(3,7,11-trimethyldodeca-2,6,10-trienyl)cyclohex-2-enone (molecular weight of 376, $C_{23}H_{36}O_4$), was obtained when compound 1 was under the condition of above 40° C. for 6 hours.

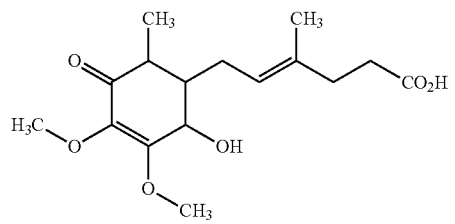

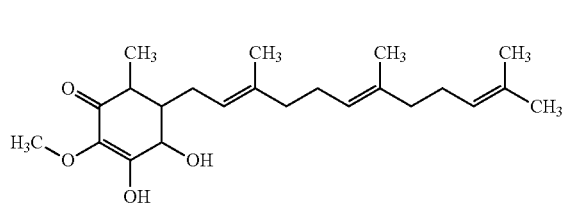

Alternatively, the exemplary compounds may be prepared from 4-hydroxy-2,3-dimethoxy-6-methylcyclohexa-2,5-dienone, or the like.

Similarly, other cyclohexenone compounds having the structure

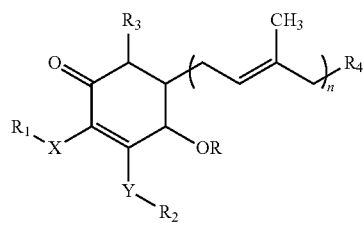

are isolated from *Antrodia camphorate* or prepared synthetically or semi-synthetically from the suitable starting materials. An ordinary skilled in the art would readily utilize appropriate conditions for such synthesis.

Example 2

Rat Smooth Muscle Cell Model

Materials and Methods

A7r5 cell line (rat aortic smooth muscle cells) was purchased from Bioresource Collection and Research Center, (Taiwan).

| | |
|---|---|
| Cell line | A7r5 (BCRC 60082) |
| Species | *Rattus norvegicus* |
| Morphology | Fibroblast |
| Description | Muscle; smooth; thoracic aorta |
| Growth Character | Adherent |
| Cell cultures | DMEM with 4 mM L-glutamine, 1.5 g/L sodium bicarbonate, 4.5 g/L glucouse + 10% FBS |
| Cell Culture Conditions | 37° C. 5% CO2 |

2.1 MTT Assay

MTT assay is commonly used to determine cell proliferation, percent of viable cells, and cytotoxicity. MTT (3[4,5-dimethylthiazol-2-yl]2,5-diphenyltetrazolium bromide) is a yellow dye, which can be absorbed by the living cells and be reduced to purplish blue formazan crystals by succinate tetrazolium reductase in mitochondria. Formazan formation can therefore be used to assess and determine the survival rate of cells. A solubilization solution (usually either dimethyl sulfoxide, an acidified ethanol solution, or a solution of the detergent sodium dodecyl sulfate in diluted hydrochloric acid) is added to dissolve the insoluble purple formazan product into a colored solution. The absorbance of this colored solution can be quantified by measuring at a certain wavelength (usually between 500 and 600 nm) by a spectrophotometer. The more surviving cells, the higher the absorbance.

The percentage of cell survival (%)=$OD$ value of experimental group÷$OD$ value of control group×100%.

Procedure

1. Adherence of cells: $2\times10^4$ cells/ml/well of A7r5 cells were seeded onto a 24-well plate and incubated at 37° C. for 24 hours.

2. Dosing: 500 ul/well different concentrations of compound 1 were pretreated in culture medium containing 1% FBS/DMEM for 20 hours. The DMEM was removed and PDGF in 1% FBS/DMEM was added and incubated at 37° C. for 24 hours.

3. MTT assay: Subsequently, in the dark environment to each well of the plates were added 50 ul/well of 5 mg/ml MTT and reacted for 3 hours. Each reaction mixture was added 500 ul/well DMSO and vibrated for 5 minute. The survival rate of cells was calculated based on the measurement of absorption at the 570 nm wavelength by ELISA reader.

2.2 Lactate Dehydrogenase (LDH) Activity Assay

Cells have plenty of lactate dehydrogenase (LDH). When cells are healthy, LDH cannot freely cross cell membrane. However, LDH is released into the surrounding medium following loss of membrane integrity resulting from either apoptosis or necrosis where the cells exhibit rapid swelling and cease its physiological mechanism. LDH activity in the culture medium is directly proportional to the number of dead cells. The cell viability can be measured quantitatively to detect absorbance by using colorimetric method at a wavelength of 492 nm. The change of the absorbance values come from the fact that LDH catalyzes the conversion of lactate to pyruvate with the concomitant production of NADH. The NADH, in the presence of diaphorase and tetrazolium salt INT, is used to drive the diaphorase-catalyzed production of red formazan product. The present experiment utilizes Cytotoxicity Assay Kit (Promega) to conduct culture medium LDH Quantitation assay.

Procedure

1. Adherence of cells: $2\times10^4$ cells/ml/well of A7r5 cells were seeded onto a 24-well plate and incubated at 37° C. for 24 hours.

2. Dosing: 500 ul/well different concentrations of compound 1 were formulated in culture medium containing 10% FBS/DMEM and incubated for 24 hours. The culture medium of each well was centrifuged for 5 minutes at 400×g and the supernatants (50 µl) were transferred into another 96-well plate.

3. LDH assay: 50 µl of substrate mixed solution was added and reacted at room temperature for 30 mins in the dark. 50 µl of Stop solution was added to terminate the reaction. Absorbance was measured by ELISA reader at the 490 nm wavelength.

2.3 Wound Scratching Test

Procedure

1. A7r5 cells ($5\times10^6$ cells/ml) were seeded onto a 6-well cell culture plate and incubated at 37° C. overnight.

2. 1×PBS was used to wash the wells twice. Compound 1 with different concentrations in DMEM culture medium containing 1% FBS was added and pretreated for 20 hours.

3. A cross-shape acellular space was created by a sterile 200 µl pipette tip and washed twice with 1×PBS.

4. After removing PBS, 2 ml PDGF in DMEM culture medium containing 1% FBS were added. The cells were photographed by a microscope at 0, 6, 12 and 24 hours, respectively from the time of adding PDGF.

Example 3

The Rat Atherosclerosis Model 3.1 Carotid Artery Ligation Model

Arteries are vessels that carry blood away from the heart. The carotid arteries are blood vessels that supply blood to the head, neck and brain. One carotid artery is position on each side of the neck. The right common carotid artery branches from the brachiocephalic artery and extends up the right side of the neck. The left common carotid artery branches from the aorta and extends up the left side of the neck. Each carotid artery branches into internal and external vessels near the top of the thyroid. Following the study by Hsing-Chun Chung (Dissertation, 2008, Southern Taiwan University), the carotid artery ligation was conducted on the left common carotid artery in mice to induce neointimal thickening.

This experiment used 8-week-old C57BL/6J male mice having about 25 g of body weight, which were purchased from National Laboratory Animal Center. These mice were maintained at the Laboratory Animal center of National Defense Medical Center on a 12 hour dark/12 hour light cycle in air conditional rooms (18-26° C., 30%-70% humidity).

1. The animals were given Compound 1 by oral gavage three days prior to the surgery and were continuously fed with Compound 1 for 28 days by oral gavage.

2. 8-week-old (C57BL/6J (B6) male mice were anesthetized with pentobarbital (50 mg/kg body weight). The left common carotid artery was ligated twice by a no. 6 silk suture at the site just proximal to the carotid bifurcation.

3. The animals were given Compound 1 after sutured. 8-10 mice of each group were sacrificed. Samples from carotid artery tissue and blood were collected and stored properly until further analysis, which included the comparative analysis of the treatment group and the control group.

3.2 Rat Atherosclerosis Model-ApoE Knock-Out Mice

Apo KO mice were purchased from Jackson Laboratory and maintained at National Laboratory Animal Center. The experiment was performed at Laboratory Animal center of National Defense Medical Center. 8-week-old ApoE KO mice were given preventive medication treatment three days prior to being fed with OpenSource diet (40% fat, 0.5% cholesterol) and continuously fed by oral gavage until sacrifice. During the period of the experiment, blood serums were collected from cheeks and the levels of cholesterol, C reactive protein (CRP) and ROS content in blood serums were measured.

Example 4

Serum Cholesterol Measurement by Cholesterol Assay Kit

Preparations of Standardized Cholesterol Sample

| No. | 200 uM Cholesterol standard (ul) | Assay buffer (ul) | Final Conc. (uM) |
|---|---|---|---|
| 1 | 0 | 1000 | 0 |
| 2 | 10 | 990 | 2 |
| 3 | 20 | 980 | 4 |
| 4 | 30 | 970 | 6 |
| 5 | 40 | 960 | 8 |
| 6 | 60 | 940 | 12 |
| 7 | 80 | 920 | 16 |
| 8 | 100 | 990 | 20 |

Procedure
1. Added 50 μl diluted cholesterol standard or 50 μl appropriately diluted serum.
2. Added 50 μl freshly prepared Assay Cocktail:
  a. 4745 μl assay buffer
  b. 150 μl cholesterol detector
  c. 50 μl HRP
  d. 50 μl cholesterol oxidase
  e. 5 μl cholesterol esterase
3. Incubated at 37° C. for 30 mins in the dark
4. Measure fluorescence by fluorescence detector (Excitation: OD 530-580 nm; Emission: 585-595 nm)

Example 5

C Reactive Protein Analysis by Enzyme-Linked Immunosorbent Assay (ELISA)

First, 200 μl/well of blocking buffer were added into 96-well ELISA plate and incubated for 1 hour at room temperature. 100 μl/well of diluted serum samples were added and incubated for 2 hours at room temperature. Then 100 μl/well of detection antibody were added and incubated for 1 hour at room temperature. Upon the completion of each incubation step mention above, the wells were washed 6 times with 400 μl/well of 0.05 PBS-T (wash buffer). Last, 100 μl/well of tetramethylbenzidine (TMB) were added and incubated for 15 minutes in the dark, and 50 μl of Stop solution were added to terminate the incubation. The absorbance of each well was read at 450 nm by ELISA reader.

Example 6

Histomorphology

Tissues dissected from live animals were immediately fixed in 10% formalin solution for about 24 hours, followed by dehydration using an automated tissue processor (Tissueprocessor, Japan). Samples were embedded with completely melted paraffin performed by dispersing console (Tissue-Tek, USA). Then the samples were chilled for 15 minutes at 4° C. to solidify. The paraffin blocks were sectioned into single cell layers in 5 μm thickness. The paraffin sections were placed in warm water bath and the paraffin sections were fished out and plated on glass slides. The slides were baked in oven at 75° C. for 30 minutes to melt paraffin. To deparaffinise, the slides were placed in xylene for 10 minutes and then immersed in 100% ethanol for 10 minutes. The rehydration steps were performed by subsequently placing the slides for 10 seconds in 95%, 85%, and 70% ethanol, followed by rinsing in running water for 5 minutes. The slices were immersed in hematoxylin solution (Surgipath Co., USA) for 2 minutes, washed with running water for 1 minute, and then immersed in acidic alcohol (1 ml concentrated HCl in 1 L 70% ethanol) for 1 second. The slides were dipped into ammonia solution for 1 second, and then washed by water for 10 minutes. The slides were incubated in Eosin solution for 90 seconds, dehydrated through 70%, 80%, 90% and 100% ethanol, and then air-dried. The slides were mounted using histological mounting media (Histomount Co. USA). The medial and neointimal thickening in the ligation-injured mouse carotid artery was examined by optical microscope.

Example 7

Evaluation of Blood Vessels

Materials
  The following materials were used.
  1. Olympus inverted phase contrast microscope
  2. CDF 480 imaging capture system
  3. Meta Imaging series 5.0
  Measurement of mouse blood vessel areas after ligation is shown in FIG. 1. EEL=external elastic lamina; IEL=internal elastic lamina; Medial area=area defined by EEL–area defined by IEL; Neointima area=area defined by IEL–Lumen area; N/M ratio=neointima area/medial area.

Example 8

Data Assessment and Statistical Analysis

Experimental data were presented as means±S.E.N represents the numbers of animal for each group. The data were analyzed by Kruskal-Wallis test. Multi-factorial and multi-group data were analyzed by ANOVA. All statistical analysis uses SPSS 12.0 (SPSS Inc. Chicago, Ill.). A P value <0.05 was considered to be statistically significant.

Results 8.1 Compound 1 Exhibits No Cytotoxicity to Smooth Muscle Cells

Potential cytotoxicity of Compound 1 to smooth muscle cells was tested. Compound 1 with different concentrations (ranged from 0 μg/ml-3 μg/ml) was individually added into A7r5 cell culture and incubated for 24 hours to examine survival rates of cells and cytotoxicity. As shown in FIGS. 2A/2B, the cytotoxic effect of Compound 1 at different concentrations on smooth muscle cells (A7r5) was determined via MTT assay (FIG. 2A) and LDH assay (FIG. 2B). These results have shown that cell purification was not affected by the drug treatment and no cytotoxcity has been observed.

8.2 Compound 1 Effective Inhibits PDGF-Stimulated Smooth Muscle Cell Proliferation at Appropriate Concentrations Effect of Compound 1 to smooth muscle cell (A7r5 cells) proliferation was investigated. Compound 1 with different concentrations (ranged from 0.01 μg/ml-3 μg/ml) was added into A7r5 cell culture. After incubating for 20 hours, platelet-derived growth factor (PDGF) was added and incubated for 24 hours to stimulate proliferation of smooth muscle cells. The effects of drugs on smooth muscle cell proliferation were observed by MTT assay and wound scratching test.

Figure 3:
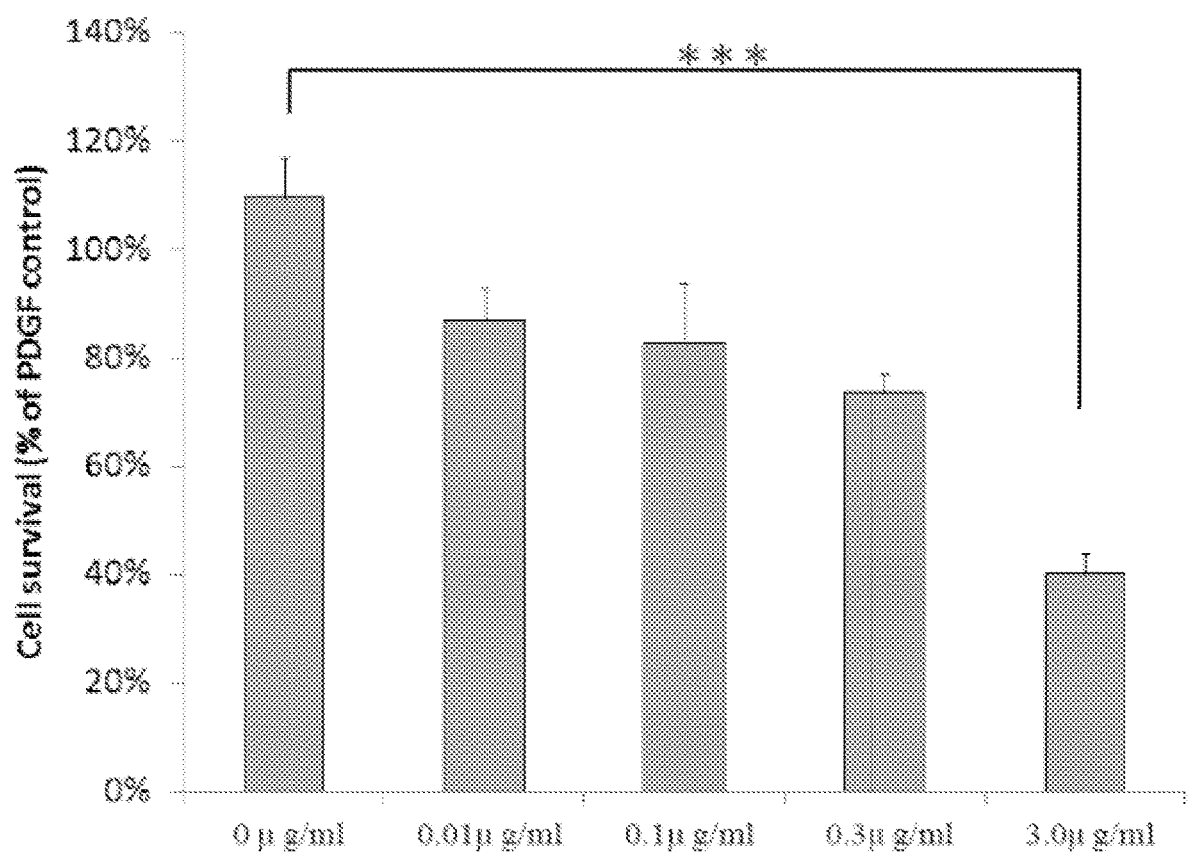
FIG. 3 shows illustrative results of Compound 1 inhibiting PDGF-treated smooth muscle cell (A7r5) proliferation at different concentrations.

MTT assay result showed that Compound 1 has significantly inhibited PDGF-stimulated smooth muscle cell proliferation. As shown in FIG. 3, MTT assay result demonstrated that after incubation with PDGF for 24 hours, smooth muscle cell proliferation was effectively reduced by about 50% in treatment groups of Compound 1 (3 µg/ml).

8.3 Compound 1 Effective Inhibits PDGF-Stimulated Smooth Muscle Cell Migration at Appropriate Concentrations The inhibition of Compound 1 on migration of smooth muscle cells (A7r5 cells) was investigated in a wound scratching test by measuring PDGF-stimulated cell migration distance. The PDGF-stimulated cell culture without Compound 1 treatment was used as positive control. The result shows that the migration of the smooth muscle cells induced by PDGF was inhibited by Compound 1 in a dose-dependent manner. As shown in FIG. 4, treatment with Compound 1 (3 µg/ml) shows about 50% of decrease in smooth muscle cell migration.

Figure 7:
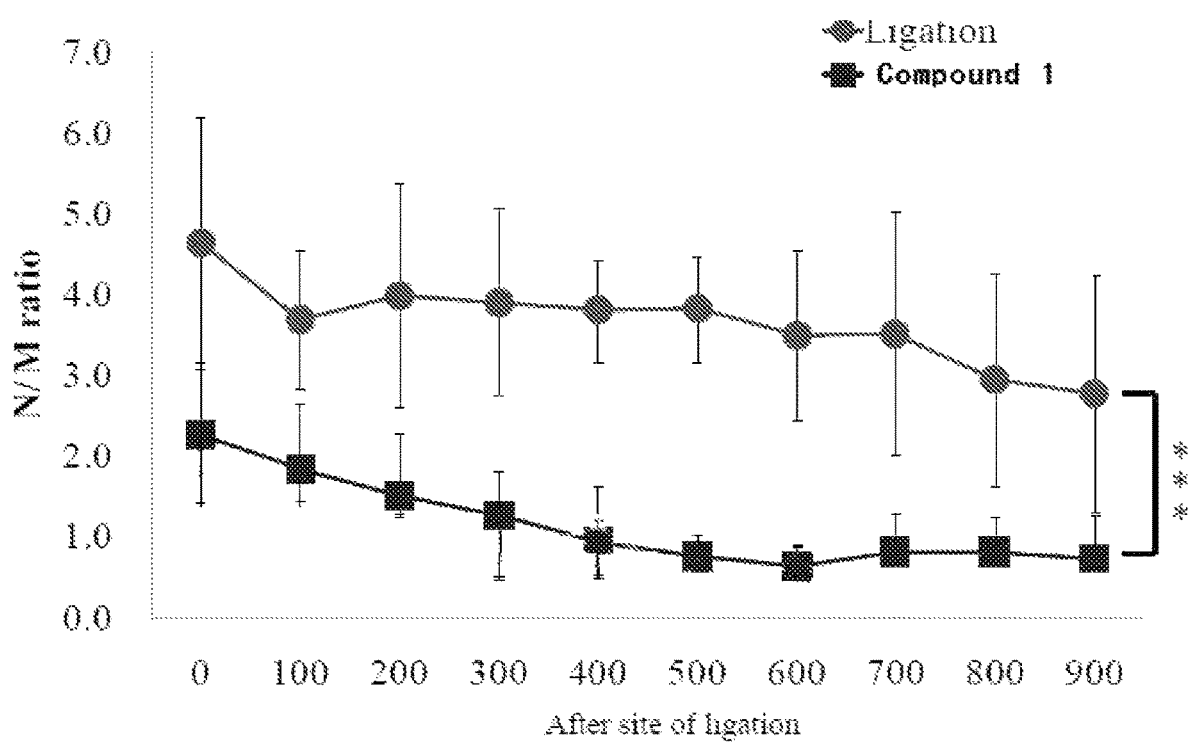
FIG. 7 shows illustrative assessment of atherosclerotic lesions with the treatment of Compound 1.

8.4 Compound 1 Effectively Reduced Neointima Formation in Mice with Carotid Artery Ligation Three days prior to the operation, the mice were oral gavage fed with Compound 1 (60 mg/kg body weight), then the neointimal thickening was induced by carotid artery ligation. The mice were continuously treated for 28 days to study the effect of Compound 1 on neointima formation. In order to study the effect of the carotid artery ligation, Hematoxylin and eosin staining was performed to examine the thickening in media area and neointima area of carotid artery after ligation, as shown in FIG. 5 and FIG. 6, respectively. The treatment efficacy was evaluated based on lumen area, neointima area, media area and neotima/media ratio (N/M ration). As shown in FIG. 7, average N/M ratio was higher than 3.0 in control mice. However, average N/M ratio was lowered to 1.0 in mice treated with Compound 1. The reduction of neointima formation was statistically significant ($p<0.001$).

Figure 8:
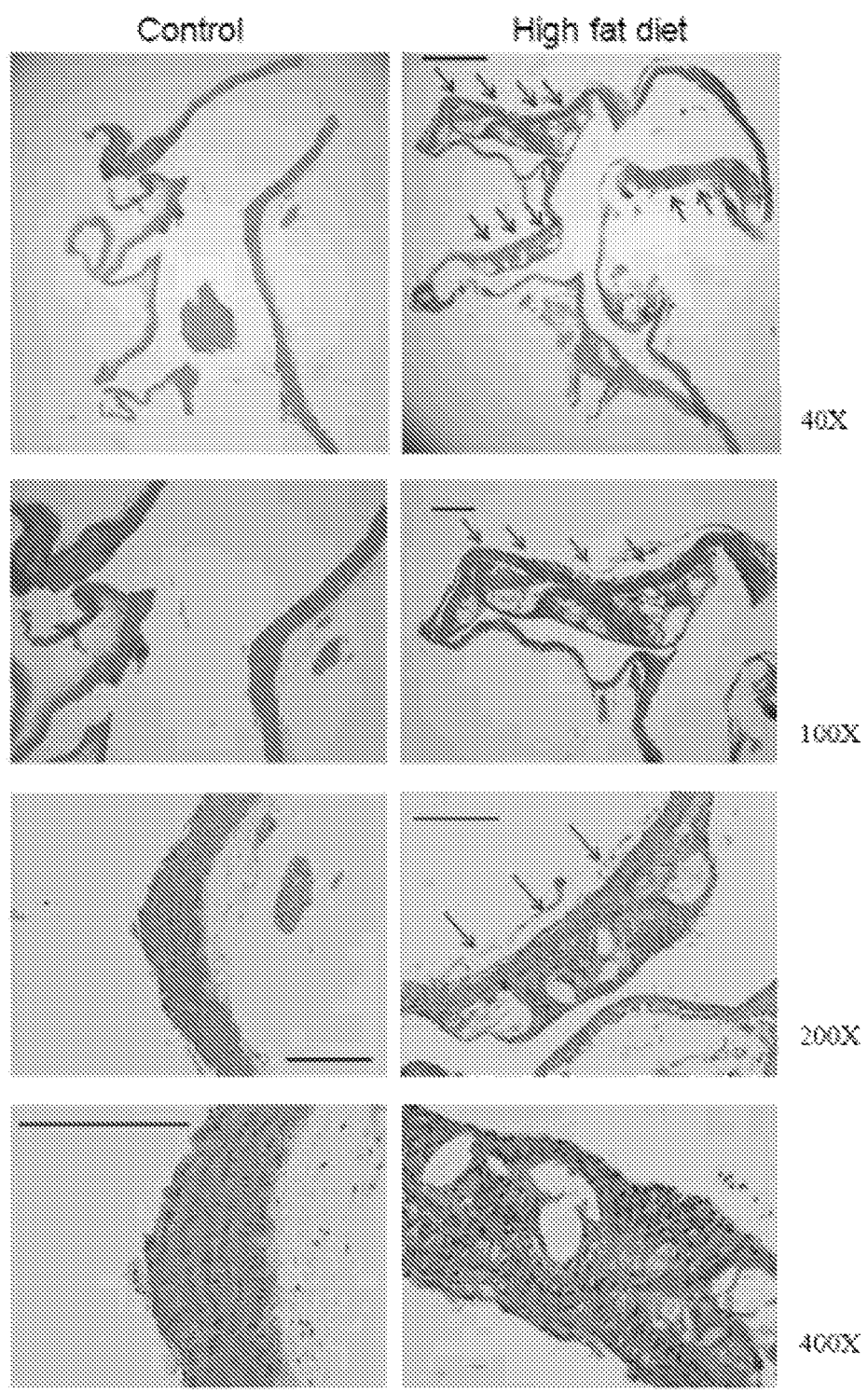
FIG. 8 shows illustrative pathologic analysis of aorta in ApoE mice fed with normal diet and high-fat diet under microscope.

8.5 Treatment of Compound 1 in the Aortic Arch of Apo KO Mice Fed with High-Fat Diet As shown in FIG. 8, fatty streaks and cholesterol deposition in aortic arch, foam cell formation, migration of smooth muscle cells and unstable fibrous plaques formation was observed in apoE-deficient mice (C57BL/6J background) fed with high fat diet. The amounts of Blood cholesterol, C-reactive protein and ROS contents were measured in the apoE-deficient mice fed high-fat diet and gavaged with Compound 1 (60 mg/kg body weight).

Figure 9:
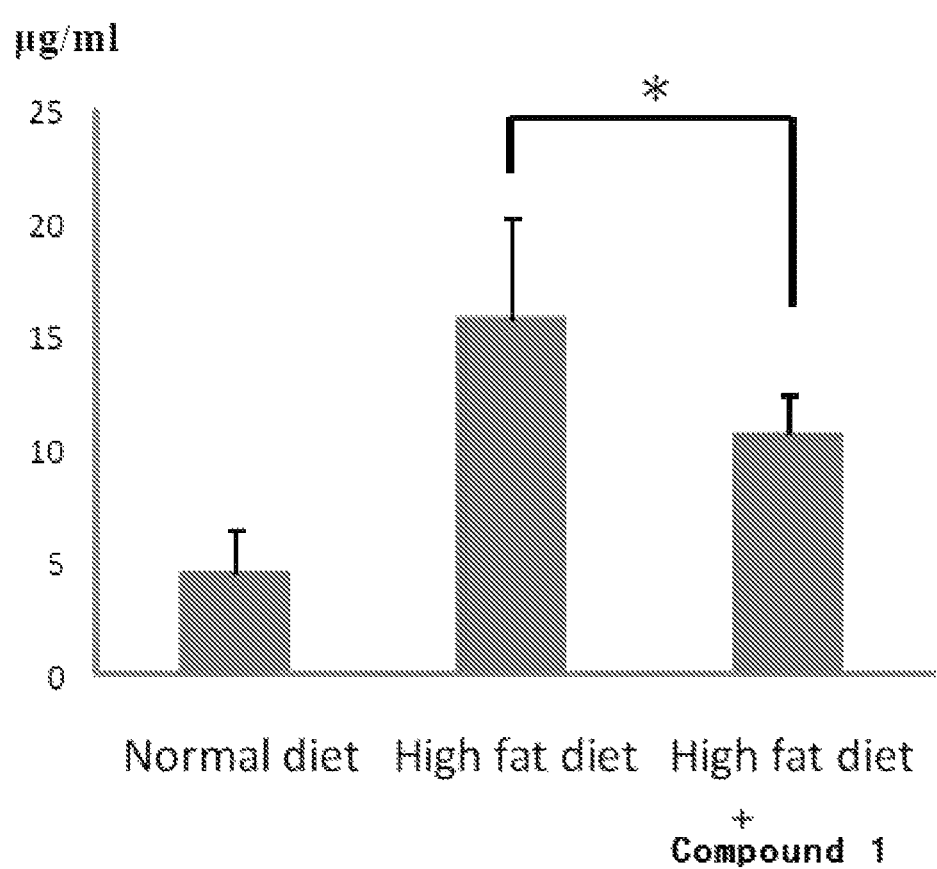
FIG. 9 shows illustrative assessment of serum C-reactive protein (CRP) levels in ApoE mice with or without Compound 1 treatment.

C-reactive protein (CRP) is a unique protein produced by the liver and was named because it reacts with the C-polysaccharide of pneumococcus. The levels of CRP rise in response to acute inflammatory diseases, bacterial infections, tissue injury or malignancy, and decline rapidly after recovery from the acute conditions. It is called as an acute phase reactant protein and is a marker for inflammation. Thus, the levels of CRP in the ApoE mice treated with Compound 1 were measured to evaluate treating inflammation by Compound 1. As shown in FIG. 9, Compound 1 significantly reduce CRP concentration in ApoE mice ($p<0.05$). Moreover, Reactive oxygen species (ROS) generation in mice treated with Compound 1 was also assessed.

Example 9

Evaluation of the Efficacy and Safety of Compound 1 in Atherosclerosis Treatment Primary Outcome Measures:
Change in neointima formation after 8 Weeks [Time Frame: Change from baseline and after 8 weeks of treatment]
Secondary Outcome Measures:
Safety of Compound 1 in dose-escalation (adverse events and serious adverse events) is measured. Timeframe is one year.
Criteria
Inclusion Criteria: subjects presenting type IIa or IIb primary hypercholesterolaemia diagnosed for at least 3 months, in a context of primary prevention with at least two associated cardiovascular risk factors and: (i) either "naive" to all lipid-lowering therapy, (ii) or treated with a statin (treatment ongoing or stopped during the previous 8 weeks).
Arms
Compound 1: Experimental. Intervention: Drug: Compound 1.
Assigned Intervention
Drug: Compound 1. Dosage form: 100 mg capsule bid×28 day cycles (Continuous treatment for a maximum of 1 year).
The results will provide if the patients who take Compound 1 can reduce neointima formation. The experiment further provides how to treat atherosclerosis.

Example 10

Preparation and Maintenance of HepG2 Cell line and Cell Culture

HepG2 cells were cultured in MEM alpha medium (Invitrogen/Gibco BRL, Grand Island, N.Y., USA). Cells were cultured at 37° C. in 5% $CO_2$ in culture media supplemented with 10% fetal bovine serum (Invitrogen/Gibco BRL) and 100 U/ml streptomycin and penicillin (Invitrogen/Gibco BRL). For treatment, cells were seeded in six-well plates at $6.25 \times 10^5$ cells/well. On the following day, the media were changed to serum-free and the cells were serum-starved for 24 h. Compound 1 was dissolved in DMSO and diluted to the required concentration with serum-free medium. Cultures were then treated with diluted Compound 1 for the indicated time periods. After treatment, cells were washed with cold phosphate-buffered saline and lysed using RIPA lysis buffer containing phosphatase and protease inhibitors.

Example 11

Detection of Gene Expression by RT-PCR

LDLR mRNA expression level was quantitative analysis by RT-PCR. For detection of hepatic LDLR mRNA, total RNA from HepG2 was extracted with TRIzol® reagent (Invitrogen, Carlsbad, Calif.) according to the manufacturer's recommendations. From 1 µg of total RNA, cDNAs were synthesized using oligo(dT) 20 primer and SuperScript III® Reverse Transcriptase (Invitrogen, Carlsbad, Calif.). PCR was done using Accupower PCR premix (Bioneer) and following primers: LDLR forward: 5' CTTT-CAACACACAACAGCAGA 3'(SEQ ID NO.1); LDLR reverse: 5' TGACAGGGCAAAGGCTAAC 3'(SEQ ID NO.2); GAPDH forward: 5' GGTATCGTGGAAGGACT-CAT 3' (SEQ ID NO.3); GAPDH reverse: 5' CCTTGCC- CACAGCCTTG 3'(SEQ ID NO.4). The PCR products intensity was quantified by densitometry using Image-Pro Plus software (Media Cybernetics, Silver Spring, Md.).

Example 12

Immunoblot Analysis

Sixty micrograms of total protein in cell lysate, which was measured using Bradford assay (Sigma-Aldrich, St. Louis, Mo.), was resolved on 12.5% SDS polyacrylamide gels. Electrophoresis was performed at a constant voltage of 180V for 50 minutes and transferred onto PVDF membrane at a constant current of 280 mA for 90 minutes. Blots were blocked with 3% BSA and probed with a 1:1,000 dilution of antibodies to phospho-p44/42 (ERK1/2)(Thr202/Tyr204) (Cell Signaling Technology, USA), p44/42MAPK(ERK1/2) (Cell Signaling Technology, USA) or β-actin (Sigma-Aldrich, St. Louis, Mo.), then horse radish-peroxidase (HRP)-conjugated secondary antibody and detected by 3,3'-diaminobenzidine (DAB) substrate kit for peroxidase (Vector Laboratories, Burlingame, Calif.). The immunoreactive bands were quantified by densitometry using Image-Pro Plus software (Media Cybernetics, Silver Spring, Md.).

Example 13

Plasma Lipoproteins in the Golden Syrian Hamster after Treatment with Compound 1

The quantitative and qualitative characteristics of the lipoprotein in the plasma of male Syrian hamsters are investigated. Male Syrian hamsters are obtained from National Laboratory Animal Center. This experiment uses sexually mature, male Syrian hamsters, weighing 100-120 g and aged 8 weeks throughout this study. These hamsters are maintained in air conditional rooms (18-26° C., 30%-70% humidity) at a 14-h light cycle. Hamsters have free access to water and food until the day before killing. Following two-week naturalization, the animals are weighted and statistically divided into groups (n=10 per group). Body weights of the animals are measured (Vibra DH-R 1500N, Japan) every week. The food consumption (g/cage) is calculated and recorded. Compound 1 is added in the food and given to the hamsters in an amount of one, two and four times more than the amount suggested by the experimental institute for 8 weeks.

Blood Samples

Blood (2-3 ml/animal) is drawn into tubes containing EDTA and gentamicin (final concentrations 1 mg/ml and 0.005%, respectively.

Blood collection schedule: At week 0 and 4, orbital sampling is utilized; at week 8, sacrifice sampling is utilized.

Blood sample handling: After resting at room temperature for 2 hours, the blood samples are centrifuged for 10 minutes at 3600 rpm to collect serum samples for analysis. After the experiment is finished at week 8, animals are anesthetized with carbon dioxide and sacrificed. Liver samples are collected, weighted, divided and stored under −80° C. for further protein and enzyme analysis. The experimental data are expressed as mean+/−standard deviation (S.D.). Data among each experimental group is analyzed by using One-way analysis of variance (ANOVA) with Duncan test for comparing the difference between each group ($p<0.05$).

Lipoprotein Isolation

Hamster and human plasma or serum lipoproteins are subfractioned on the basis of their hydrated density by the isopycnic ultracentrifugal density gradient procedure known in the art. Gradients are constructed in Ultraclear tubes of the Beckman SW41-Ti rotor (or the like). On completion of ultracentrifugation, fractions of 0.4 ml are collected successively. Lipoprotein fractions are exhaustively dialyzed in Spectrapor tubing for 24 hours at 4° C. against a solution containing NaCl, HEPES, NaN3 EDTA and gentamycin, pH 7.4.

The concentrations of lipids in pooled hamster plasma are recorded.

Example 14

Effects of Compound 1 on Serum LDL Cholesterol Concentrations

The principal objective of this study is to investigate the effects of a cyclohexenone compound (Compound 1) on LDL-cholesterol levels in healthy subjects with moderate hypercholesterolemia.

Study type: Interventional
Study Design: Allocation: Randomized
Endpoint Classification: Safety/Efficacy Study
Intervention Model: Parallel Assignment
Masking: Double Blind (Subject, Caregiver, Investigator)
Primary Purpose Treatment
Primary Outcome Measures:
Change from Baseline in blood LDL-cholesterol levels at 4 months [Time Frame: 4 months] [Designated as safety issue: No]
Secondary Outcome Measures:
Change from Baseline in blood Vit. C, Vit. E, polyphenols and MDA levels at 4 months [Time Frame: 4 months] [Designated as safety issue: No]

| Arms | Assigned Interventions |
| --- | --- |
| Experimental: Compound 1 | Drug: Compound 1<br>200 mg once daily for 1 week followed by 100 mg twice daily for 1 week followed by 50 mg twice daily for 4 weeks |
| Placebo Comparator:<br>Placebo | Drug: Placebo<br>Placebo once daily for 1 week followed by placebo twice daily for 5 weeks. |

Eligibility
 Ages Eligible for Study: 18 Years to 55 Years
 Genders Eligible for Study: Both
 Accepts Healthy Volunteers: Yes
Criteria
 Inclusion Criteria: Males or females, age 18-55
 Subject has a stable weight for at least three months before the start of the study
 Subject able and willing to comply with the protocol and agreeing to give their consent in writing
 Subject affiliated with a social security scheme
 Subject willing to be included in the national register of volunteers who lend themselves to biomedical research Example 15

Parenteral Formulation

To prepare a parenteral pharmaceutical composition suitable for administration by injection, 100 mg of a compound or its salt described herein is dissolved in DMSO and then mixed with 10 mL of 0.9% sterile saline. The mixture is incorporated into a dosage unit form suitable for administration by injection.

Example 16

Oral Formulation

To prepare a pharmaceutical composition for oral delivery, 100 mg of an exemplary Compound 1 was mixed with 100 mg of corn oil. The mixture was incorporated into an oral dosage unit in a capsule, which is suitable for oral administration.

In some instances, 100 mg of a compound described herein is mixed with 750 mg of starch. The mixture is incorporated into an oral dosage unit for, such as a hard gelatin capsule, which is suitable for oral administration.

Example 17

Sublingual (Hard Lozenge) Formulation

To prepare a pharmaceutical composition for buccal delivery, such as a hard lozenge, mix 100 mg of a compound described herein, with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 18

Inhalation Composition

To prepare a pharmaceutical composition for inhalation delivery, 20 mg of a compound described herein is mixed with 50 mg of anhydrous citric acid and 100 mL of 0.9% sodium chloride solution. The mixture is incorporated into an inhalation delivery unit, such as a nebulizer, which is suitable for inhalation administration.

Example 19

Rectal Gel Formulation

To prepare a pharmaceutical composition for rectal delivery, 100 mg of a compound described herein is mixed with 2.5 g of methylcelluose (1500 mPa), 100 mg of methylparapen, 5 g of glycerin and 100 mL of purified water. The resulting gel mixture is then incorporated into rectal delivery units, such as syringes, which are suitable for rectal administration.

Example 20

Topical Gel Composition

To prepare a pharmaceutical topical gel composition, 100 mg of a compound described herein is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Example 21

Ophthalmic Solution Composition

To prepare a pharmaceutical ophthalmic solution composition, 100 mg of a compound described herein is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for the treatment of atherosclerosis comprising administering to a human a therapeutically effective amount of a cyclohexenone compound having the structure:

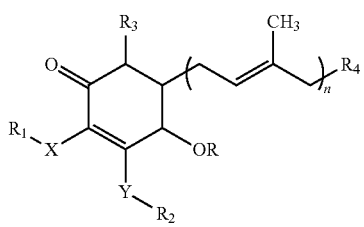

wherein each of X and Y independently is oxygen, $NR_5$ or sulfur;

R is a hydrogen or $C(=O)C_1$-$C_8$alkyl;

each of $R_1$, $R_2$ and $R_3$ independently is a hydrogen, methyl or $(CH_2)_m$—$CH_3$;

$R_4$ is $C_1$-$C_8$alkyl, $C_2$-$C_8$alkenyl, $C_2$-$C_8$alkynyl, optionally substituted with one or more substituents selected from $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl; $R_5$ is a hydrogen or $C_1$-$C_8$alkyl;

m=1-12; and n=1-12; or a pharmaceutically acceptable salt, metabolite, solvate or prodrug thereof.

2. The method of claim 1, wherein said compound inhibits PDGF-stimulated smooth muscle cell proliferation or migration, or reduce neointima formation.

3. The method of claim 1, wherein the atherosclerosis is caused by coronary artery disease, aneurysm, arteriosclerosis, myocardial infarction, embolism, stroke, thrombosis, angina, vascular plaque inflammation, vascular plaque rupture, Kawasaki disease, calcification or inflammation.

4. The method of claim 1, wherein said compound lowers low-density lipoprotein (LDL) cholesterol, or maintains a normal low-density lipoprotein (LDL) cholesterol level in the human.

5. The method of claim 1, wherein said compound inhibits the production or progression of one or more atherosclerotic lesions within the vasculature of the human.

6. The method of claim 5, wherein the vasculature comprises a cardiac artery, or an aorta.

7. The method of claim 1, wherein said cyclohexenone compound, or a pharmaceutically acceptable salt, metabolite, solvate or prodrug thereof, is administered parenterally, orally, intravenously, or by injection.

8. The method of claim 1, wherein said compound is isolated from *Antrodia camphorata*, or prepared synthetically or semisynthetically.

9. The method of claim 1, wherein R is a hydrogen, $C(=O)C_3H_8$, $C(=O)C_2H_5$, or $C(=O)CH_3$.

10. The method of claim 1, wherein each of $R_1$, $R_2$ and $R_3$ independently is a hydrogen, methyl, ethyl, propyl, butyl, pentyl, hexyl, heptyl, or octyl.

11. The method of claim 10, wherein each of $R_1$ or $R_2$ independently is a hydrogen or methyl.

12. The method of claim 1, wherein $R_4$ is $C_1$-$C_8$alkyl optionally substituted with one or more substituents selected from $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl.

13. The method of claim 12, wherein $R_4$ is $CH_2CH=C(CH_3)_2$.

14. The method of claim 1, wherein said compound is

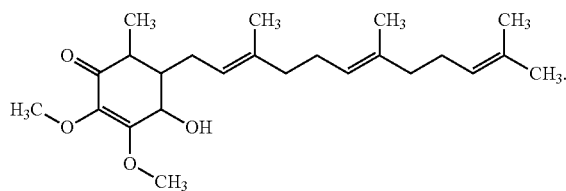 [SMILES: COC1=C(OC)C(O)C(C/C=C(\C)CC/C=C(\C)CCC=C(C)C)C(C)C1=O]

15. The method of claim 1, wherein the amount is in a range from 50 mg to 300 mg per dose.

16. A method for preventing or treating an inflammation-related arteriosclerotic vascular disease, or reducing C-reactive protein, or lowering low-density lipoprotein (LDL) cholesterol, or maintaining a normal low-density lipoprotein (LDL) cholesterol level in a subject comprising administering to the subject a therapeutically effective amount of a compound having the structure:

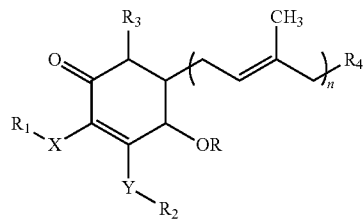

wherein each of X and Y independently is oxygen, $NR_5$ or sulfur;
R is a hydrogen or $C(=O)C_1$-$C_8$alkyl;
each of $R_1$, $R_2$ and $R_3$ independently is a hydrogen, methyl or $(CH_2)_m$—$CH_3$;
$R_4$ is $C_1$-$C_8$alkyl, $C_2$-$C_8$alkenyl, $C_2$-$C_8$alkynyl, optionally substituted with one or more substituents selected from $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;
$R_5$ is a hydrogen or $C_1$-$C_8$alkyl;
$R_7$ is a $C_1$-$C_8$alkyl, $OR_5$ or $NR_5R_6$;
m=1-12; and
n=1-12; or a pharmaceutically acceptable salt, metabolite, solvate or prodrug thereof.

17. The method of claim 16, wherein R is a hydrogen, $C(=O)C_3H_8$, $C(=O)C_2H_5$, or $C(=O)CH_3$, each of $R_1$, $R_2$ and $R_3$ independently is a hydrogen, methyl, ethyl, propyl, butyl, pentyl, hexyl, heptyl, or octyl, and $R_4$ is $C_1$-$C_8$alkyl optionally substituted with one or more substituents selected from $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl.

18. The method of claim 16, wherein said compound induces low-density lipoprotein (LDL) receptor expression in the subject.

19. The method of claim 16, wherein said compound increases hepatic LDLR expression.

* * * * *